United States Patent [19]
Chenivesse et al.

[11] Patent Number: 5,989,881
[45] Date of Patent: Nov. 23, 1999

[54] **NUCLEIC ACID MOLECULES ENCODING DELTA-5,7-STEROL, DELTA-7 REDUCTASE FROM *ARABIDOPSIS THALIANA***

[75] Inventors: Xavier Chenivesse, Ivry sur Seine; Catherine Duport, Bures sur Yvette; Eric Lecain, Cachan; Denis Pompon, Gif sur Yvette, all of France

[73] Assignee: Hoechst Marion Roussel, France

[21] Appl. No.: 08/783,202

[22] Filed: Jan. 14, 1997

Related U.S. Application Data

[62] Division of application No. 08/601,435, Feb. 12, 1996, Pat. No. 5,759,801.

[30] Foreign Application Priority Data

Feb. 15, 1995 [FR] France ................................ 95 01723
Jun. 1, 1995 [FR] France ................................ 95 06517

[51] Int. Cl.$^6$ .............................. C12N 9/02; C12N 1/16; C12N 15/00; C07H 21/04
[52] U.S. Cl. ................ 435/189; 435/254.11; 435/254.2; 435/320.1; 435/52; 435/71.1; 536/23.2; 536/23.6
[58] Field of Search .................... 435/69.1, 71.1, 435/52, 189, 254.11, 254.2, 320.1

[56] References Cited

U.S. PATENT DOCUMENTS 5,547,868  8/1996  Miller et al. ............................. 435/189

FOREIGN PATENT DOCUMENTS 0360361  3/1990  European Pat. Off. .

OTHER PUBLICATIONS

Kissel et al (1989) Biochem Biophys Acta 1006:227–236 "Molecular Clonins and Expression of cDNA for Rat Pancreatic Cholesterol Esterase".

Corey et al (1993) PNAS 90:11628–11632 "Isolation of an Arabidopsis Thallang Gene Encoding Cycloartenol Synthase by Functional Expression in a Yeast . . . ".

Ashman, et al (1991) Lipids 26:628–632 "Cloning Disruption of the Yeast (C–8 Sterol Isomerase Gene".

Ritter et al (1970) Bioc Biophs Res Comm 38:921–929 "Purfication . . . ".

Newman et al (1994) Plant Physiol 106:1241–1255 "Genes Galore . . . ".

*Primary Examiner*—Ponnathapu Achutamurthy
*Assistant Examiner*—Tekchand Saidha
*Attorney, Agent, or Firm*—Bierman, Muserlian and Lucas

[57] ABSTRACT

A nucleic acid sequence containing a sequence coding for a protein having a delta-5,7 sterol, delta-7 reductase activity, said nucleic acid being a DNA or an RNA, production process, strains of transformed yeasts and uses thereof.

11 Claims, 26 Drawing Sheets

```
GTGTGAGTAA TTTAGGTCAA CACAGATCAG AATCTGAGGC TTTGGCCGAG ACGAAGAGAA     60

AACCAGAAGA AGAAA ATG GCG GAG ACT GTA CAT TCT CCG ATC GTT ACT TAC    111
            Met Ala Glu Thr Val His Ser Pro Ile Val Thr Tyr
            1               5                   10

GCA TCG ATG TTA TCG CTT CTC GCC TTC TGT CCA CCT TTC GTC ATT CTC    159
Ala Ser Met Leu Ser Leu Leu Ala Phe Cys Pro Pro Phe Val Ile Leu
         15                  20                  25

CTA TGG TAC ACA ATG GTT CAT CAG GAT GGT TCT GTT ACT CAG ACC TTT    207
Leu Trp Tyr Thr Met Val His Gln Asp Gly Ser Val Thr Gln Thr Phe
     30                  35                  40

GGC TTC TTT TGG GAG AAT GGA GTT CAA GGA CTT ATC AAC ATA TGG CCA    255
Gly Phe Phe Trp Glu Asn Gly Val Gln Gly Leu Ile Asn Ile Trp Pro
 45                  50                  55                  60

AGA CCC ACT TTG ATT CTT TGG AAA ATT ATA TTT TGC TAT GGA GCA TTT    303
Arg Pro Thr Leu Ile Leu Trp Lys Ile Ile Phe Cys Tyr Gly Ala Phe
         65                  70                  75

GAA GCT ATT CTT CAG CTG CCT CTG CCT GGT TAC AAG GCC AAT GGT CTG GCT    351
Glu Ala Ile Leu Gln Leu Pro Leu Pro Gly Lys Tyr Lys Ala Asn Gly Leu Ala
     80                  85                  90

ATA TCT CCA GCC GGA AAC CGA GTT TAC AAG GCC AAT GGT CTG GCT    399
Ile Ser Pro Ala Gly Asn Arg Pro Val Tyr Lys Ala Asn Gly Leu Ala
 95                  100                 105

GCT TAC TTT GTG ACA CTA GCA ACC CAT CTT GGT TGG TGG TTT GGA    447
Ala Tyr Phe Val Thr Leu Ala Thr His Leu Gly Trp Trp Phe Gly
 110                 115                 120
```

FIG. 3A

| | | | | | | | | | | | | | | | | |
|---|---|---|---|---|---|---|---|---|---|---|---|---|---|---|---|---|
| ATC | TTC | AAC | CCT | GCA | ATT | GTC | TAT | GAT | CAC | TTG | GGT | GAA | ATA | TTT | TCG | |
| Ile | Phe | Asn | Pro | Ala | Ile | Val | Tyr | Asp | His | Leu | Gly | Glu | Ile | Phe | Ser | 495 |
| 125 | | | | | 130 | | | | | 135 | | | | | 140 | |
| GCA | CTA | ATA | TTC | GGA | AGC | TTC | ATA | TTT | TGT | GTT | TTG | TAC | ATA | AAA | | |
| Ala | Leu | Ile | Phe | Gly | Ser | Phe | Ile | Phe | Cys | Val | Leu | Tyr | Ile | Lys | | 543 |
| | | | | 145 | | | | | 150 | | | | 155 | | | |
| GGC | CAT | GTT | GCA | CCT | TCA | TCA | AGT | GAC | TCT | GGT | TCA | TGT | AAC | CTA | | |
| Gly | His | Val | Ala | Pro | Ser | Ser | Ser | Asp | Ser | Gly | Ser | Cys | Asn | Leu | | 591 |
| | | | 160 | | | | | 165 | | | | | 170 | | | |
| ATA | ATT | GAC | TAT | TGG | CCT | GCA | ATG | GGC | CCT | ATT | GGT | AAG | | | | |
| Ile | Ile | Asp | Tyr | Trp | Pro | Ala | Met | Gly | Pro | Ile | Gly | Lys | | | 639 |
| | | 175 | | | | | 180 | | | | 185 | | | | | |
| AGC | TTT | GAC | ATC | AAG | ACG | TTT | TAC | CCT | AGA | ATG | ATG | TCT | | | | |
| Ser | Phe | Asp | Ile | Lys | Thr | Phe | Tyr | Pro | Arg | Met | Met | Ser | | | 687 |
| | 190 | | | | | 195 | | | | 200 | | | | | | |
| TGG | GCA | ATC | CTT | GCA | GTC | ACG | TAC | ATA | CAG | GGA | TAT | GAA | ATA | AAT | | |
| Trp | Ala | Ile | Leu | Ala | Val | Thr | Tyr | Ile | Gln | Gly | Tyr | Glu | Ile | Asn | | 735 |
| 205 | | | | 210 | | | | 215 | | | | | 220 | | | |
| GGC | AAA | GTA | TCT | GAT | ATG | CTG | GTG | AAC | ACC | ATC | CTG | ATG | CTG | GTG | | |
| Gly | Lys | Val | Ser | Asp | Met | Leu | Val | Asn | Thr | Ile | Leu | Met | Leu | Val | | 783 |
| | | | 225 | | | | 230 | | | | 235 | | | | | |
| TAT | GTC | ACA | AAA | TTC | TTC | TGG | GAA | GCT | GGT | TAT | TGG | AAC | ACC | ATG | | |
| Tyr | Val | Thr | Lys | Phe | Phe | Trp | Glu | Ala | Gly | Tyr | Trp | Asn | Thr | Met | | 831 |
| | | 240 | | | | | 245 | | | | | 250 | | | | |

FIG. 3B

```
GAC ATT GCA CAT GAC CGA GCT GGA TTC TAT ATA TGC TGG GGT TGT CTA          879
Asp Ile Ala His Asp Arg Ala Gly Phe Tyr Ile Cys Trp Gly Cys Leu
        255             260             265

GTG TGG GTG CCT TCT GTC TAC ACT TCT CCA GGC ATG TAC CTT GTG AAC          927
Val Trp Val Pro Ser Val Tyr Thr Ser Pro Gly Met Tyr Leu Val Asn
    270             275             280

CAC CCC GTC GAA CTC GGA CTC ACT CAG TTG GCA ATA TAC ATT CTC GTT GCA     975
His Pro Val Glu Leu Gly Leu Thr Gln Leu Ala Ile Tyr Ile Leu Val Ala
    285             290             295             300

GGA ATT CTG TGC ATT TAC AAG TAT GAT AGA TGT TAC ATT CTC GTT CAA         1023
Gly Ile Leu Cys Ile Tyr Lys Tyr Asp Arg Cys Tyr Ile Leu Val Gln
            305             310             315

GAG TTC AGG AGG ACA AAC GGG AAA TGT GAT AGA CAA AGG GCC CCG             1071
Glu Phe Arg Arg Thr Asn Gly Lys Cys Asp Arg Gln Arg Ala Pro
        320             325             330

TCA AAG ATT GTG GCG TCG TAT ACT ACA TCT GGT GAA ACT AAA ACT             1119
Ser Lys Ile Val Ala Ser Tyr Thr Thr Ser Gly Glu Thr Lys Thr
    335             340             345

AGT CTT CTC TTA ACG TCT GGA TGG TGG TTG GCT GCA CGT CAT TTC CAT         1167
Ser Leu Leu Leu Thr Ser Gly Trp Trp Leu Ala Ala Arg His Phe His
    350             355             360

TAT GTT CCT GAG ATC TTA AGT GCT TTC TTC TGG ACC GTA CCG GCT CTC         1215
Tyr Val Pro Glu Ile Leu Ser Ala Phe Phe Trp Thr Val Pro Ala Leu
365         370             375             380
```

FIG. 3C

```
TTC GAT AAC TTC TTG GCA TAC TTC TAC GTC CTC ACC CTT CTC TTT    1263
Phe Asp Asn Phe Leu Ala Tyr Phe Tyr Val Leu Thr Leu Leu Phe
                385                 390                 395

GAT CGA GCC AAG AGA GAC GAT GAC CGA TGC CGA TCA AAG TAT GGG AAA    1311
Asp Arg Ala Lys Arg Asp Asp Asp Arg Cys Arg Ser Lys Tyr Gly Lys
            400                 405                 410

TAT TGG AAG CTG TAT TGT GAG AAA GTC AAA TAC AGG ATC ATT CCG GGA    1359
Tyr Trp Lys Leu Tyr Cys Glu Lys Val Lys Tyr Arg Ile Ile Pro Gly
        415                 420                 425

ATT TAT TGATTGTAAC GAAGTCTGTT GTTCTCATTT TCTACTTATT ACGTTAATTC    1415
Ile Tyr
    430

GAACGTTGGA ATCATCAAAA GACCGAGCCA AAACAAAAAT GCAAATTGAT GCGATAGACA    1475

TTCTTTTGCT GAAAAAAAAA A    1496
```

FIG. 3D

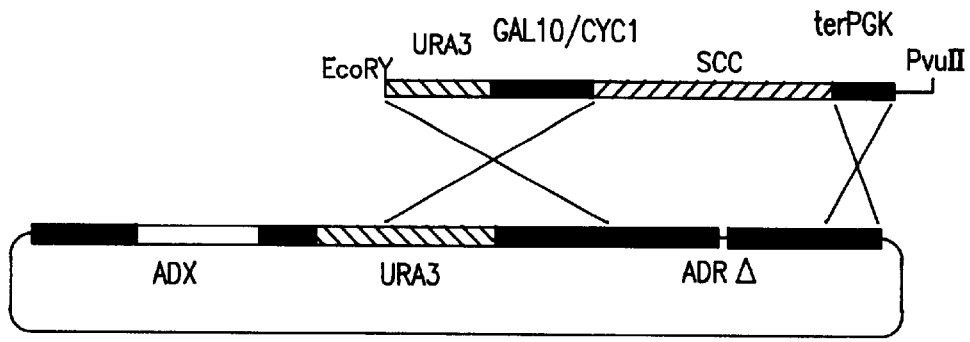
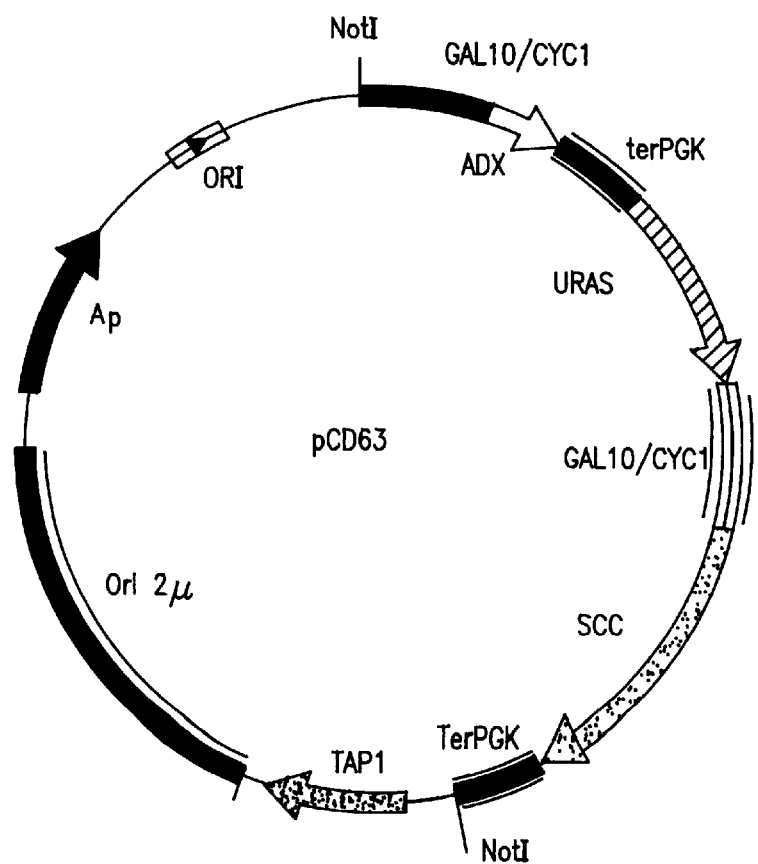
FIG. 11B

NUCLEIC ACID MOLECULES ENCODING DELTA-5,7-STEROL, DELTA-7 REDUCTASE FROM *ARABIDOPSIS THALIANA*

PRIOR APPLICATION

This application is a division of U.S. patent application Ser. No. 601,435 filed Feb. 12, 1996 now U.S. Pat. No. 5,759,801.

STATE OF THE ART

Delta-5,7 sterol, delta-7 reductase (E.C.1.3.1.21) is a microsomal enzyme whose presence has been revealed by its activity in homogenates of rat's liver (Dempsey et al., Methods Enzymol., Vol. 15, pp. 501–514, 1969) as well as in plant preparations of *Zea mays* (Taton et al., Biochem. Biophys. Res. Commun., Vol. 181, pp. 465–473, 1991). This reductase is dependent on NADPH and reduces 7-dehydrocholesterol to cholesterol in vitro.

Sterols are the main constituents of the membranes in eucaryotes but show structural differences depending on the species. In the cells of eucaryotes such as yeasts, the principal sterol is ergosterol which contains a double unsaturation in position C-5 and C-7, a branched side chain in position C-24 and an unsaturation in position C-22 while in mammals, cholesterol is characterized by an unsaturation in position C-5 and a saturated side chain. Sitosterol, stigmasterol and campesterol, which represent the most common sterols in plants, have a branched but saturated side chain and, as with the sterols of vertebrates, do not have an unsaturation in position C-7. The enzyme responsible for this difference in structure of the sterol nucleus is delta-5,7 sterol, delta-7 reductase. Delta-5,7 sterol, delta-7 reductase has never been purified to homogeneity and only a partial purification has been described (Dempsey et al.; Taton et al., already quoted). The protein has not been characterized by its physical-cheinical properties. No information on the sequence of the protein and no antibody directed against it have been described. Furthermore, an apparent deficiency in 7-dehydrocholesterol reductase has been described in man associated with RSH/Smith-Lemli-Opitz (SLO) syndrome (Opitz et al., Am. J. Med. Genet., Vol. 50, pp. 326–338, 1994).

Cloning of a cDNA coding for delta-5,7 sterol, delta-7 reductase, which may enable the sequence of the corresponding protein to be identified as well as the characterization of the human gene or a congenital deficiency of it to be revealed, is not therefore achievable by known methods which make use for example of hybridization and/or immunological detection techniques. The obtaining of inventive screening methods allowing cloning to be carried out, particularly in the absence of information about the protein, is therefore particularly sought-after.

Ergosterol, the principal sterol of the membranes of fungi, contains a pair of conjugated double bonds in position C-5,7 which confers an antimycotic activity on compounds of the family of polyenes such as nystatin (Bittman et al., J. Biol. Chem., Vol. 260, pp.2884–2889, 1985). The strong dependency of the action of nystatin on the membrane concentration of unsaturated sterols in position C-5,7 has allowed the selection of mutant strains vis-a-vis accumulated sterols in S. cerevisiae (Molzahn et al., J. Gen. Microbiol., Vol. 72, pp. 339–348, 1972). Thus, the mutants erg2 and erg3 accumulate sterols which do not have conjugated double bonds in position C-5,7 because of a deficiency in sterol delta-8,7 isomerase (Ashman et al., Lipids, Vol. 26, pp. 628, 1991) and in sterol delta-5 dehydrogenase (Arthinton et al., Gene, Vol. 102, p. 39, 1991) respectively. Such mutants are viable because ergosterol, the principal natural sterol of yeast, can be replaced under certain conditions by different substitution sterols including cholesterol.

OBJECTS OF THE INVENTION

It is an object of the invention to provide a cDNA sequence coding for an *A. thaliana* protein having a delta-5,7 sterol, delta-7 reductase activity, cloning processes and processes for reducing sterols unsaturated in position C-7.

It is another object of the invention to provide a process for the production of pregnenolone.

These and other objects and advantages of the invention will become obvious from the following detailed description.

THE INVENTION

The nucleic acid sequence of the invention contains a sequence coding for a protein having a delta-5,7 sterol, delta-7 reductase, activity, said nucleic acid being a DNA or an RNA.

The advantage of increasing the resistance to nystatin of yeast strains enriched with sterols not having the double unsaturation in position C-5,7 was perceived by the inventors for cloning a cDNA coding for a heterologous protein having a delta-5,7 sterol, delta-7 reductase activity with a screening method using a metabolic interference in S. cerevisiae. The success of this approach which offers the advantage of being independent of knowing the DNA sequences or the protein as well as a detection solely based on the enzymatic activity, is not however foreseeable due to the many technical difficulties to be overcome.

A first limitation comes from the fact that the way nystatin works is not entirely elucidated (Parks et al., CRC Critical Reviews in Microbiology, pp. 301–304, 1978). For example, the low specificity of the selection by nystatin is foreseeable due to the indirect nature of it which leads in yeast to the selection of spontaneous genomic mutations such as the erg mutants (Molzahn et al. already quoted) or genomic mutations involving resistances independent of the sterol pathway. Similarly, cells transformed by a gene library can express heterologous genes conferring a resistance to nystatin unrelated to the sterol pathway.

Another example of the expected limitation relates to the fact that the heterologous protein could be weakly active in the cell, leading to the absence of or to a low resistance to nystatin, for example, for one of the following reasons:
1) the gene coding for delta-5,7 sterol, delta-7 reductase is weakly expressed;
2) the protein is weakly or not active because of poor folding or as a result of an incorrect subcellular orientation;
3) the plant protein does not recognize the yeast's own sterols as substrates or
4) the sterols which can be substrates are in the esterified form or stored in vesicles and are not in contact with the enzyme. It can therefore be anticipated that the sterols accumulated in this way escape the action of delta-5,7 sterol, delta-7 reductase which, in eucaryotes, is reputed to be localized in the microsomes.

The present invention relates to the cloning of a cDNA of A. thaliana coding for a protein having a delta-5,7 sterol, delta-7 reductase activity, designated delta-7Red, according to a cloning process carried out in a yeast by metabolic interference based on the resistance to nystatin. The delta-7Red protein allows the sterols having an unsaturation in position C-7 to be reduced by a biological reduction process, which in addition provides an advantageous solution to the problem of the selective reduction in position C-7 of sterols or steroids having a double unsaturation in position C-5,7 which the reduction methods using chemical routes do not allow.

The invention also relates to transformed yeast cells expressing the delta-7Red which, in a surprising manner, accumulate products saturated in position C-7 and optionally saturated in position C-22 which, contrary to ergosterol, are substrates of the restriction enzyme of the side chain of cholesterol, i.e. cytochrome $P_{450}SCC$.

These unexpected properties allow the use of the transformed yeasts of the invention in a preparation process for sterols or steroids having an industrial and/or pharmacological use, in particular the preparation of pregnenolone by biological oxidation of endogenic yeast sterols, reduced in position C-7, by cytochrome $P_{450}SCC$ ($P_{450}SCC$) in the presence of adrenodoxin reductase (ADR) and adrenodoxin (ADX). The transformed yeasts of the invention can be also used in a preparation process for intermediate steroids in the metabolization route of cholesterol into hydrocortisone in mammals and other vertebrates. This use has the advantage of allowing the preparation of hydrocortisone or its intermediates in a biological oxidation process which does not require the use of an exogenic sterol such as cholesterol as the initial substrate and thus by-passing the problem of the penetration of a sterol into the yeast whose impermeability to exogenous sterols under aerobiosis conditions has been described (Lorentz et al., J. Bacteriology, pp. 981–985, 1986).

The invention also relates to the use of nucleic sequences obtained using the cloning process of the invention. An RNA or DNA sequence coding for delta-5,7 sterol, delta-7 reductase can be used for the diagnosis or the treatment of affections implicating the product of the gene of delta-5,7 sterol, delta-7 reductase. For example, a deficiency in delta-5,7 sterol, delta-7 reductase which converts 7-dehydrocholesterol into cholesterol is presumed to be implicated in RSH/SLO syndrome. Thus, a human DNA sequence can be used as a probe for diagnosing a deficiency in delta-5,7 sterol, delta-7 reductase and can also be used in gene therapy to correct such a deficiency.

Therefore, an object of the invention is a nucleic acid sequence containing a sequence coding for a protein having a delta-5,7 sterol, delta-7 reductase activity, said nucleic acid being a DNA or an RNA and in particular being a cDNA. The delta-5,7 sterol, delta-7 reductase activity can be revealed for example using an enzymatic test in vitro described further on in the experimental part.

A more particular object of the invention is a cDNA sequence in which the coding sequence codes for a protein of *A. thaliana* having a delta-5,7 sterol, delta-7 reductase activity and having the nucleotide sequence of the sequence SEQ ID No. 1:

```
GTGTGAGTAA TTTAGGTCAA CACAGATCAG AATCTGAGGC TTTGGCCGAG ACGAAGAGAA      60

AAGCAGAAGA AGAAA ATG GCG GAG ACT GTA CAT TCT CCG ATC GTT ACT TAC      111
           Met Ala Glu Thr Val His Ser Pro Ile Val Thr Tyr
             1               5                  10

GCA TCG ATG TTA TCG CTT CTC GCC TTC TGT CCA CCT TTC GTC ATT CTC      159
Ala Ser Met Leu Ser Leu Leu Ala Phe Cys Pro Pro Phe Val Ile Leu
         15              20                  25

CTA TGG TAC ACA ATG GTT CAT CAG GAT GGT TCT GTT ACT CAG ACC TTT      207
Leu Trp Tyr Thr Met Val His Gln Asp Gly Ser Val Thr Gln Thr Phe
     30              35                  40

GGC TTC TTT TGG GAG AAT GGA GTT CAA GGA CTT ATC AAC ATA TGG CCA      255
Gly Phe Phe Trp Glu Asn Gly Val Gln Gly Leu Ile Asn Ile Trp Pro
 45              50                  55                  60

AGC CCC ACT TTG ATT GCT TGG AAA ATT ATA TTT TGC TAT GGA GCA TTT
Arg Pro Thr Leu Ile Ile Ala Trp Lys Ile Phe Cys Tyr Gly Ala Phe
                 65                  70                  75

GAA GCT ATT CTT CAG CTG CTT CTG CCT GGT AAA AGA GTT GAG GGT CCA      351
Glu Ala Ile Leu Gln Leu Leu Leu Pro Gly Lys Arg Val Glu Gly Pro
                 80                  85                  90

ATA TCT CCA GCC GGA AAC CGA CCA GTT TAC AAG GCC AAT GGT CTG GCT      399
Ile Ser Pro Ala Gly Asn Arg Pro Val Tyr Lys Ala Asn Gly Leu Ala
             95                 100                 105

GCT TAC TTT GTG ACA CTA GCA ACC CAT CTT GGT CTT TGG TGG TTT GGA      447
Ala Tyr Phe Val Thr Leu Ala Thr His Leu Gly Leu Trp Trp Phe Gly
         110                 115                 120

ATC TTC AAC CCT GCA ATT GTC TAT GAT CAC TTG GGT GAA ATA TTT TCG      495
Ile Phe Asn Pro Ala Ile Val Tyr Asp His Leu Gly Glu Ile Phe Ser
125                 130                 135                 140

GCA CTA ATA TTC GGA AGC TTC ATA TTT TGT GTT TTG TTG TAC ATA AAA      543
Ala Leu Ile Phe Gly Ser Phe Ile Phe Cys Val Leu Leu Tyr Ile Lys
                 145                 150                 155

GGC CAT GTT GCA CCT TCA TCA AGT GAC TCT GGT TCA TGT GGT AAC CTA      591
Gly His Val Ala Pro Ser Ser Ser Asp Ser Gly Ser Cys Gly Asn Leu
             160                 165                 170
```

```
ATA ATT GAC TTC TAT TGG GGC ATG GAG TTG TAC CCT CGA ATT GGT AAG         639
Ile Ile Asp Phe Tyr Trp Gly Met Glu Leu Tyr Pro Arg Ile Gly Lys
        175                 180                 185

AGC TTT GAC ATC AAG GTG TTT ACT AAT TGC AGA TTC GGA ATG ATG TCT         687
Ser Phe Asp Ile Lys Val Phe Thr Asn Cys Arg Phe Gly Met Met Ser
        190                 195                 200

TGG GCA GTT CTT GCA GTC ACG TAC TGC ATA AAA CAG TAT GAA ATA AAT         735
Trp Ala Val Leu Ala Val Thr Tyr Cys Ile Lys Gln Tyr Glu Ile Asn
205                 210                 215                 220

GGC AAA GTA TCT GAT TCA ATG CTG GTG AAC ACC ATC CTG ATG CTG GTG         783
Gly Lys Val Ser Asp Ser Met Leu Val Asn Thr Ile Leu Met Leu Val
                225                 230                 235

TAT GTC ACA AAA TTC TTC TGG TGG GAA GCT GGT TAT TGG AAC ACC ATG         831
Tyr Val Thr Lys Phe Phe Trp Trp Glu Ala Gly Tyr Trp Asn Thr Met
                240                 245                 250

GAC ATT GCA CAT GAC CGA GCT GGA TTC TAT ATA TGC TGG GGT TGT CTA         879
Asp Ile Ala His Asp Arg Ala Gly Phe Tyr Ile Cys Trp Gly Cys Leu
                255                 260                 265

GTG TGG GTG CCT TCT GTC TAC ACT TCT CCA GGC ATG TAC CTT GTG AAC         927
Val Trp Val Pro Ser Val Tyr Thr Ser Pro Gly Met Tyr Leu Val Asn
        270                 275                 280

CAC CCC GTC GAA CTC GGA ACT CAG TTG GCA ATA TAC ATT CTC GTT GCA         975
His Pro Val Glu Leu Gly Thr Gln Leu Ala Ile Tyr Ile Leu Val Ala
285                 290                 295                 300

GGA ATT CTG TGC ATT TAC ATA AAG TAT GAC TGT GAT AGA CAA AGG CAA        1023
Gly Ile Leu Cys Ile Tyr Ile Lys Tyr Asp Cys Asp Arg Gln Arg Gln
                305                 310                 315

GAG TTC AGG AGG ACA AAC GGG AAA TGT TTG GTT TGG GGA AGA GCC CCG        1071
Glu Phe Arg Arg Thr Asn Gly Lys Cys Leu Val Trp Gly Arg Ala Pro
                320                 325                 330

TCA AAG ATT GTG GCG TCG TAT ACT ACA ACA TCT GGT GAA ACT AAA ACT        1119
Ser Lys Ile Val Ala Ser Tyr Thr Thr Thr Ser Gly Glu Thr Lys Thr
                335                 340                 345

AGT CTT CTC TTA ACG TCT GGA TGG TGG GGA TTG GCT CGT CAT TTC CAT        1167
Ser Leu Leu Leu Thr Ser Gly Trp Trp Gly Leu Ala Arg His Phe His
        350                 355                 360

TAT GTT CCT GAG ATC TTA AGT GCT TTC TTC TGG ACC GTA CCG GCT CTC        1215
Tyr Val Pro Glu Ile Leu Ser Ala Phe Phe Trp Thr Val Pro Ala Leu
365                 370                 375                 380

TTC GAT AAC TTC TTG GCA TAC TTC TAC GTC CTC ACC CTT CTT CTC TTT        1263
Phe Asp Asn Phe Leu Ala Tyr Phe Tyr Val Leu Thr Leu Leu Leu Phe
                385                 390                 395

GAT CGA GCC AAG AGA GAC GAT GAC CGA TGC CGA TCA AAG TAT GGG AAA        1311
Asp Arg Ala Lys Arg Asp Asp Asp Arg Cys Arg Ser Lys Tyr Gly Lys
                400                 405                 410

TAT TGG AAG CTG TAT TGT GAG AAA GTC AAA TAC AGG ATC ATT CCG GGA        1359
Tyr Trp Lys Leu Tyr Cys Glu Lys Val Lys Tyr Arg Ile Ile Pro Gly
        415                 420                 425

ATT TAT TGATTGTAAC GAAGTCTGTT GTTCTCATTT TCTACTTATT ACGTTAATTC        1415
Ile Tyr
    430

GAACGTTGGA ATCATCAAAA GACCGAGCCA AAACAAAAAT GCAAATTGAT GCGATAGACA    1475

TTCTTTTGCT GAAAAAAAAA A                                              1496
``` as well as the allelic variants of this sequence.

The above cDNA sequence which codes for a protein having 430 amino acids corresponding to the sequence shown in FIG. 3 (SEQ ID No. 2) is a cDNA sequence which can be obtained for example by cloning in a yeast, starting from an A. thaliana expression library, by using a screening method based on the appearance of a resistance of the yeast to nystatin, according to the operating conditions, a detailed description of which is given further on.

REFERRING NOW TO THE DRAWINGS

FIGS. 3a to 3e shows the nucleotide sequence of the CDNA delta-7Red (SEQ ID No. 1) and the corresponding amino acid sequence (SEQ ID No. 2).

Figure 4:
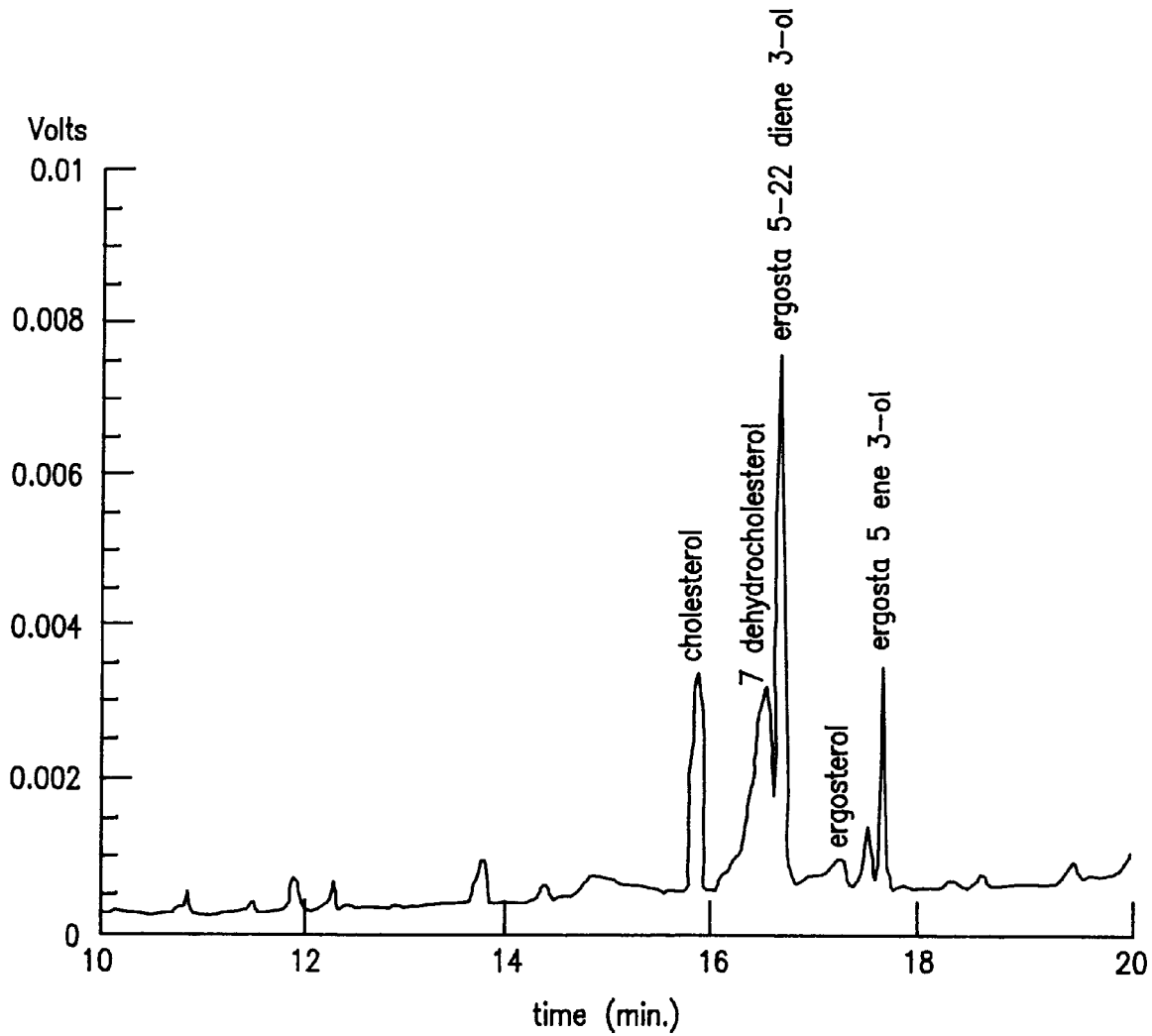

FIG. 4 is a graph of the measurement in vitro of the delta-5,7 sterol, delta-7 reductase activity of a microsomal fraction of FY1679 transformed with the inducible expression vector "delta-7/V8". Analysis was carried out with GC and it shows the transformation of the substrate 7-dehydrocholesterol (RT=16.528) into cholesterol (RT= 15.887) in the presence of the endogenic sterols 5,22 diene 3-ol (RT=16.682); ergosterol (RT=17.249);

ergosta-5-ene3-ol (RT=17.664).

Figure 5A:
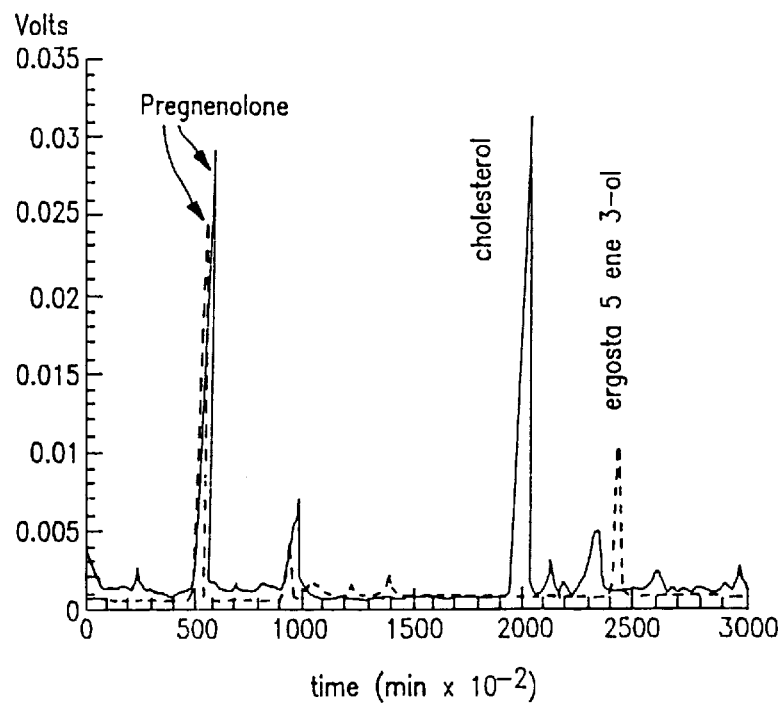
Figure 5B:
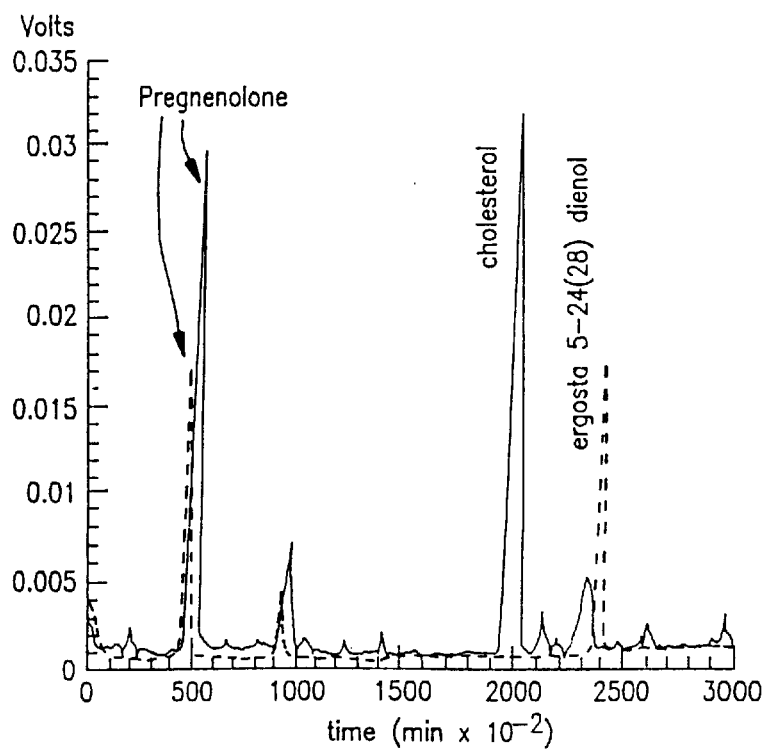
Figure 5C:
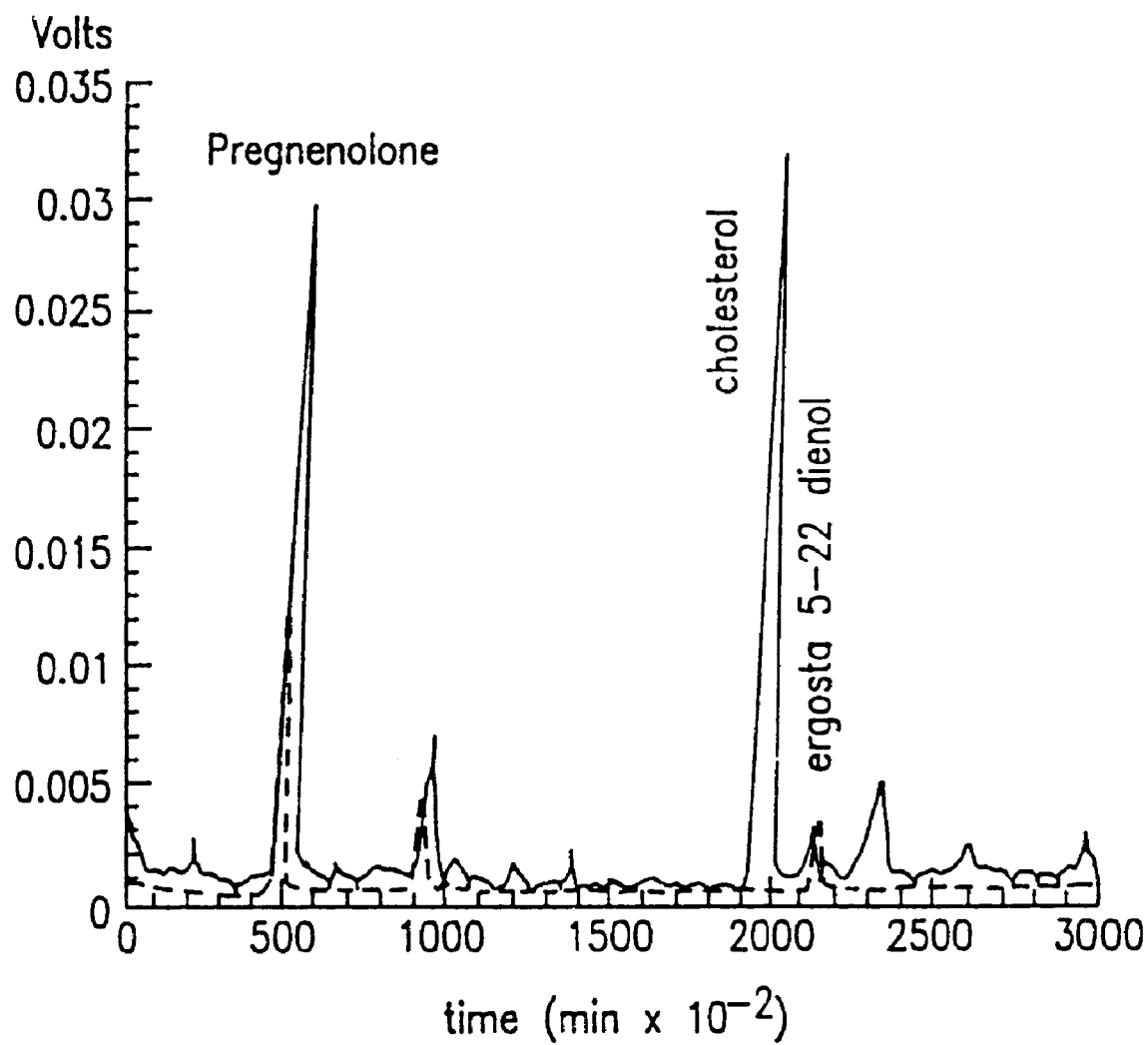

FIGS. 5 is a graph of the production of pregnenolone in vitro by cleavage of ergosta 5-ene 3-ol (FIG. 5a) ergosta 5,24(28) diene 3-ol (FIG. 5b) or ergosta 5,22 diene 3-ol (FIG. 5c) purified from a transformed yeast expressing delta-7Red, then incubated with $P_{450}SCC$, ADX and ADR. Analysis is carried out by GC compared with a control cleavage of cholesterol (full line).

Figure 6A:
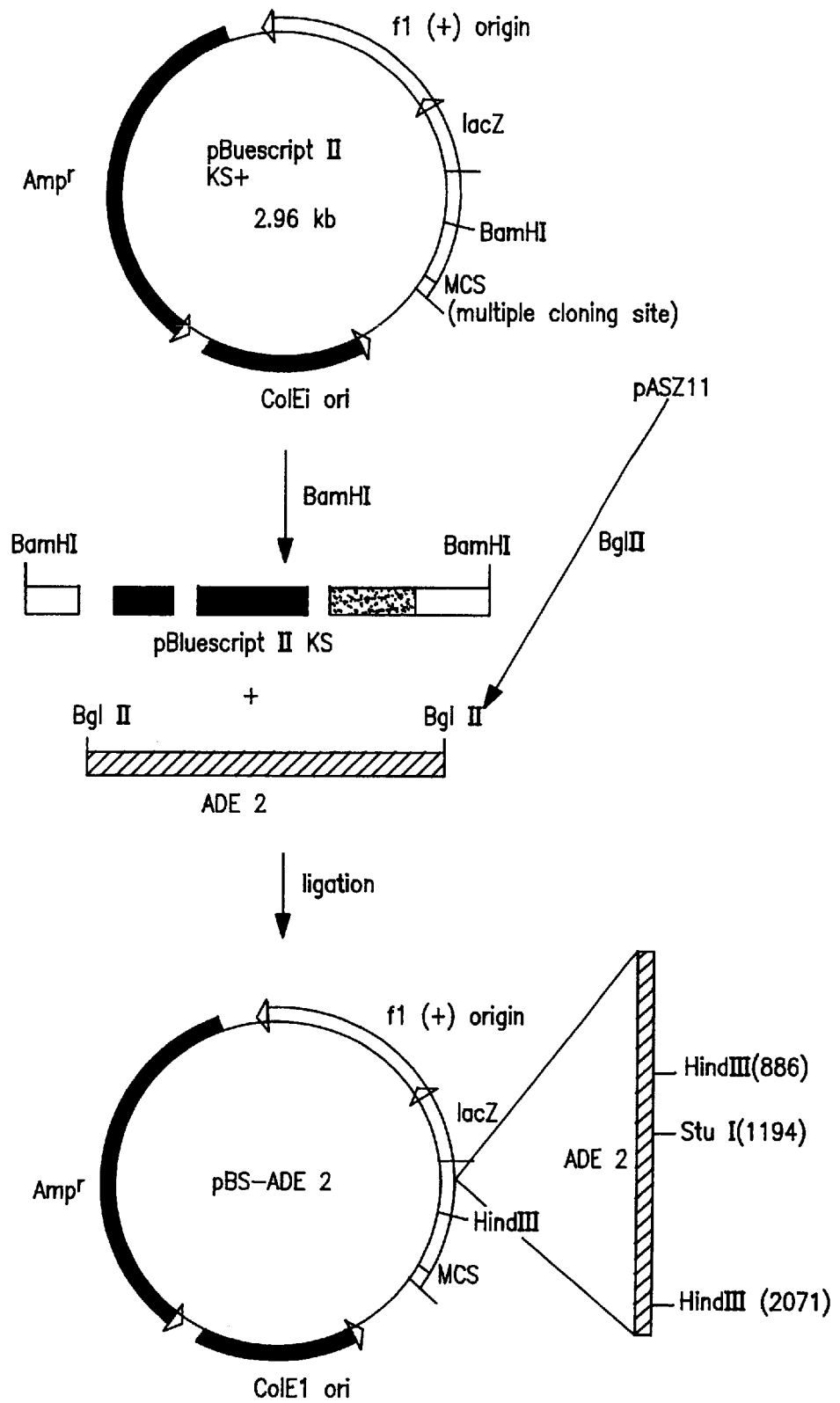
Figure 6B:
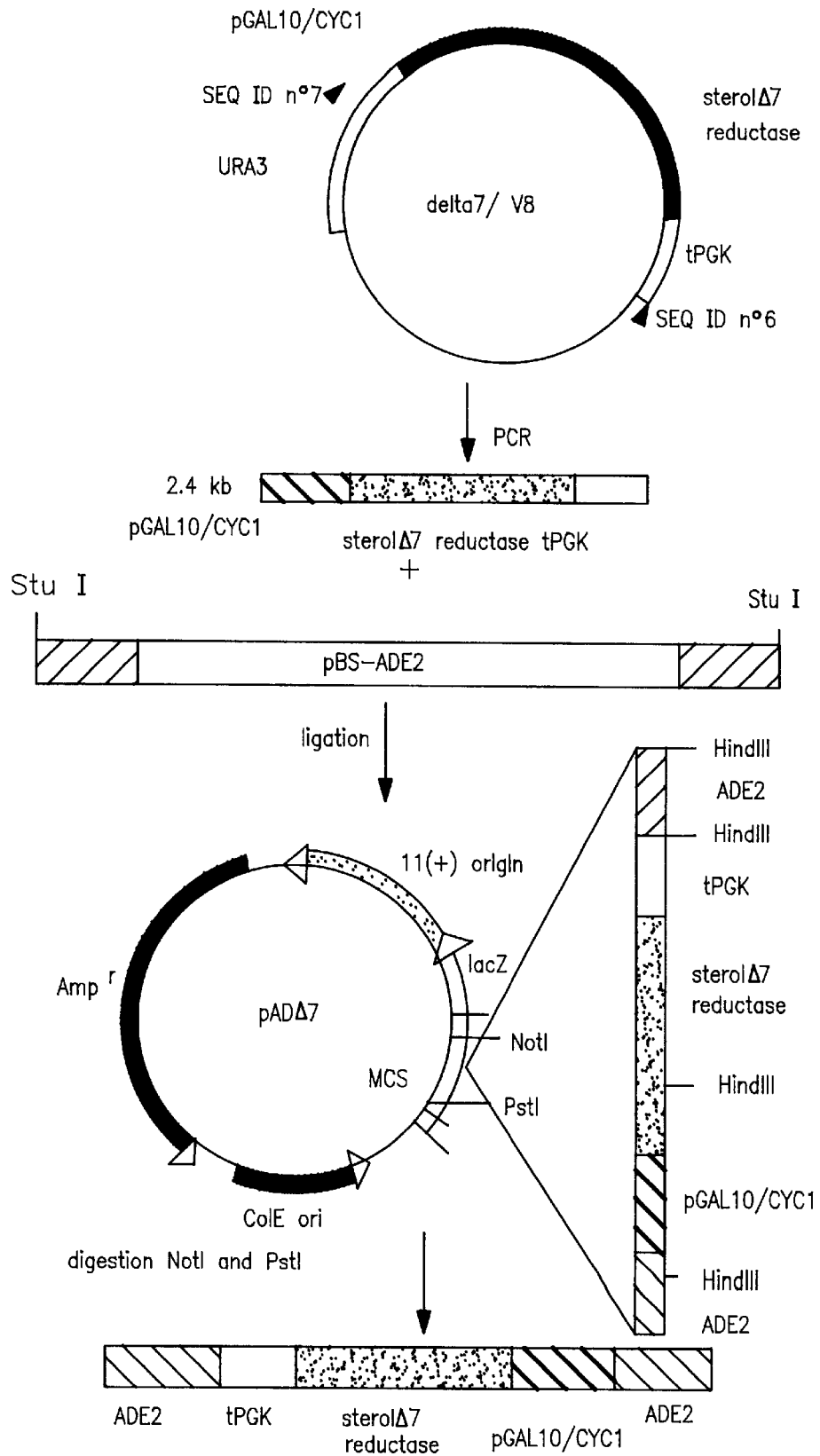

FIGS. 6a and 6b illustrate the construction of the integrative plasmid pADdelta-7 allowing the integration of the cDNA coding for the delta-7Red (sterol Δ-7 reductase) at locus ADE2.

Figure 7:
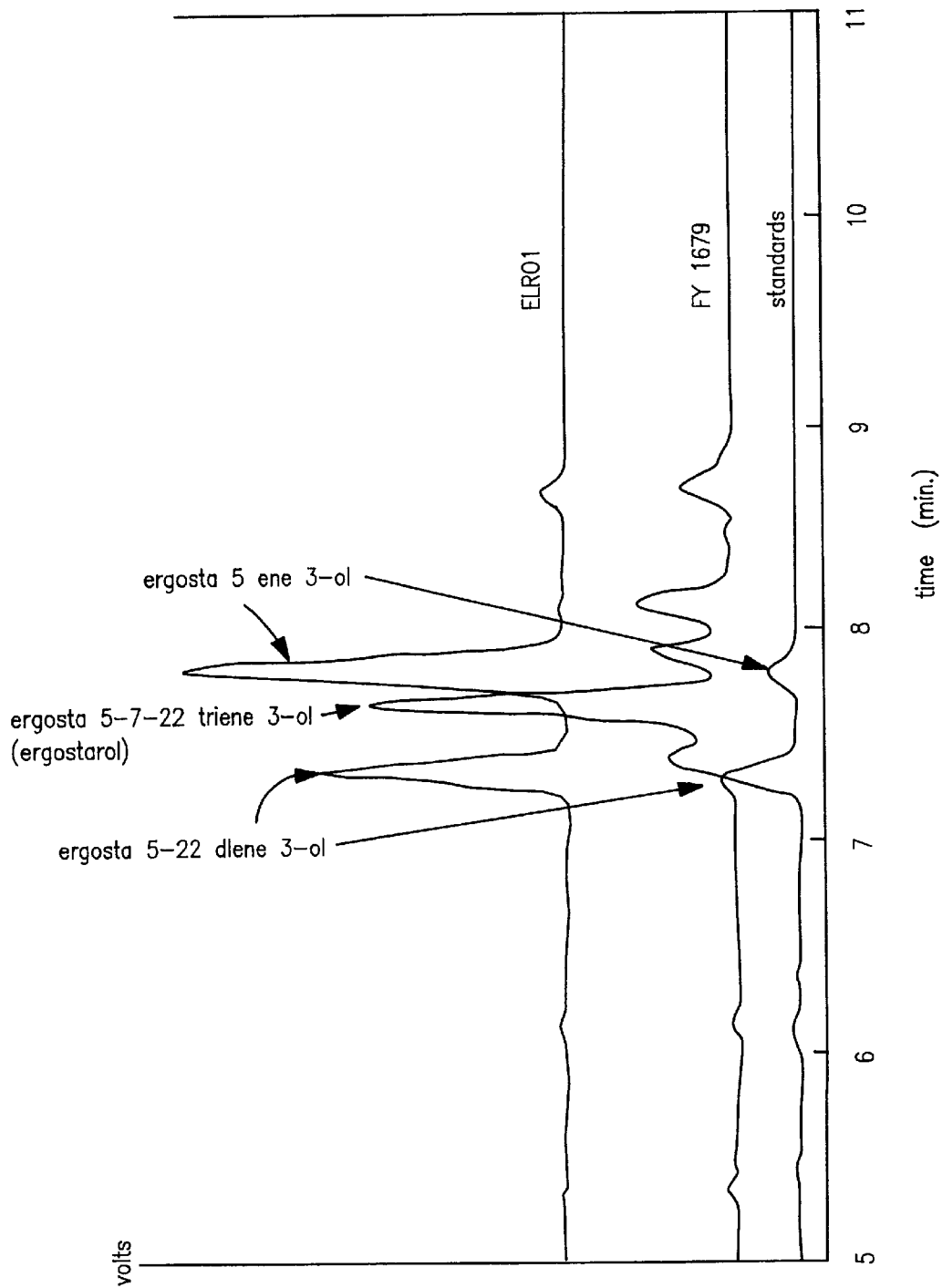

FIG. 7 is a graph of the analysis by GC of the total sterols extracted by alkaline saponification of the strain FY1679 and the integrated strain ELR01 cultured in the presence of galactose.

Figure 8:
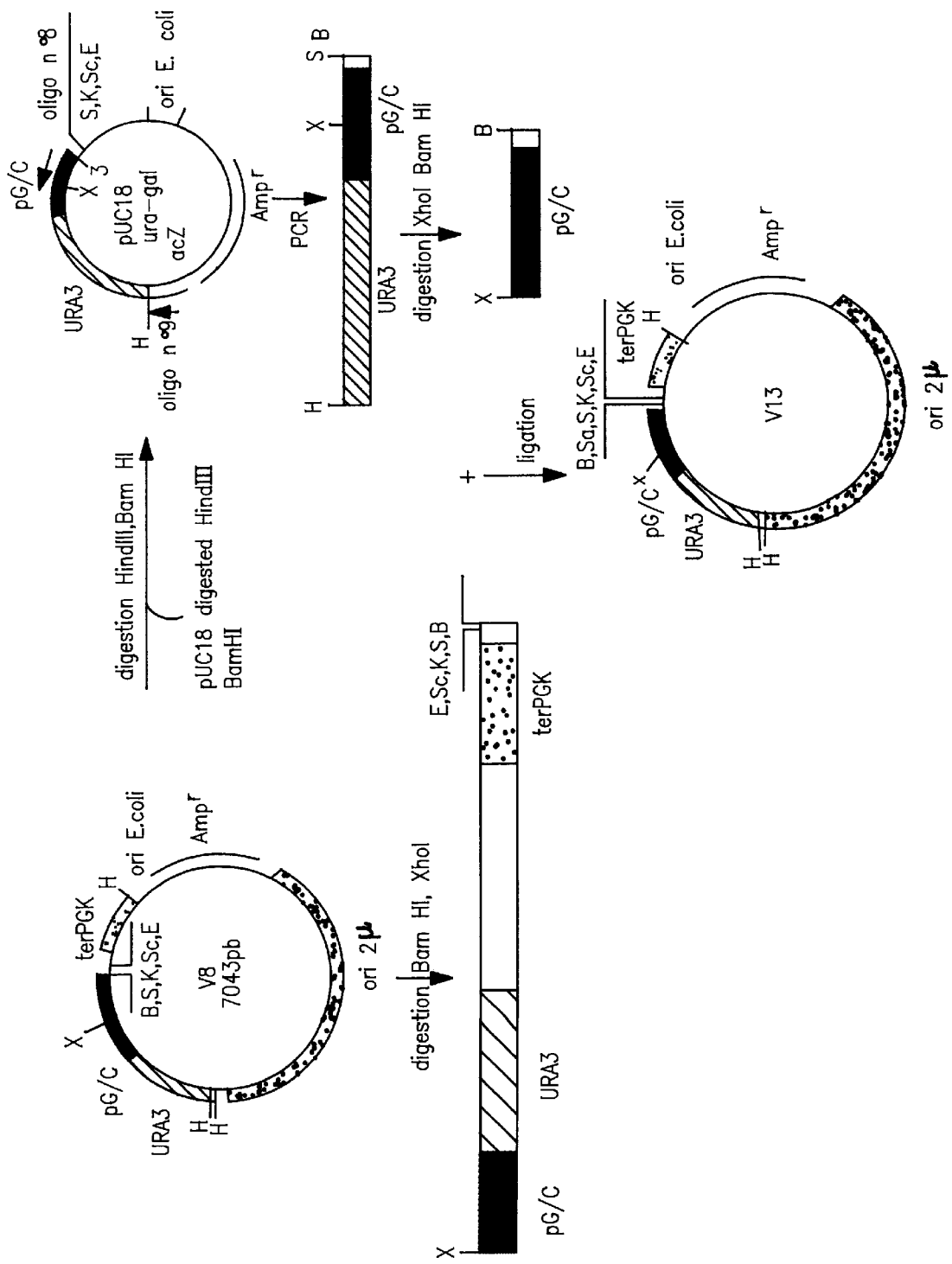

FIG. 8 schematizes the construction of the shuttle vector E. coli-S. cerevisiae V13 containing a single SalI (Sa) site in the multiple cloning site.

Figure 9A:
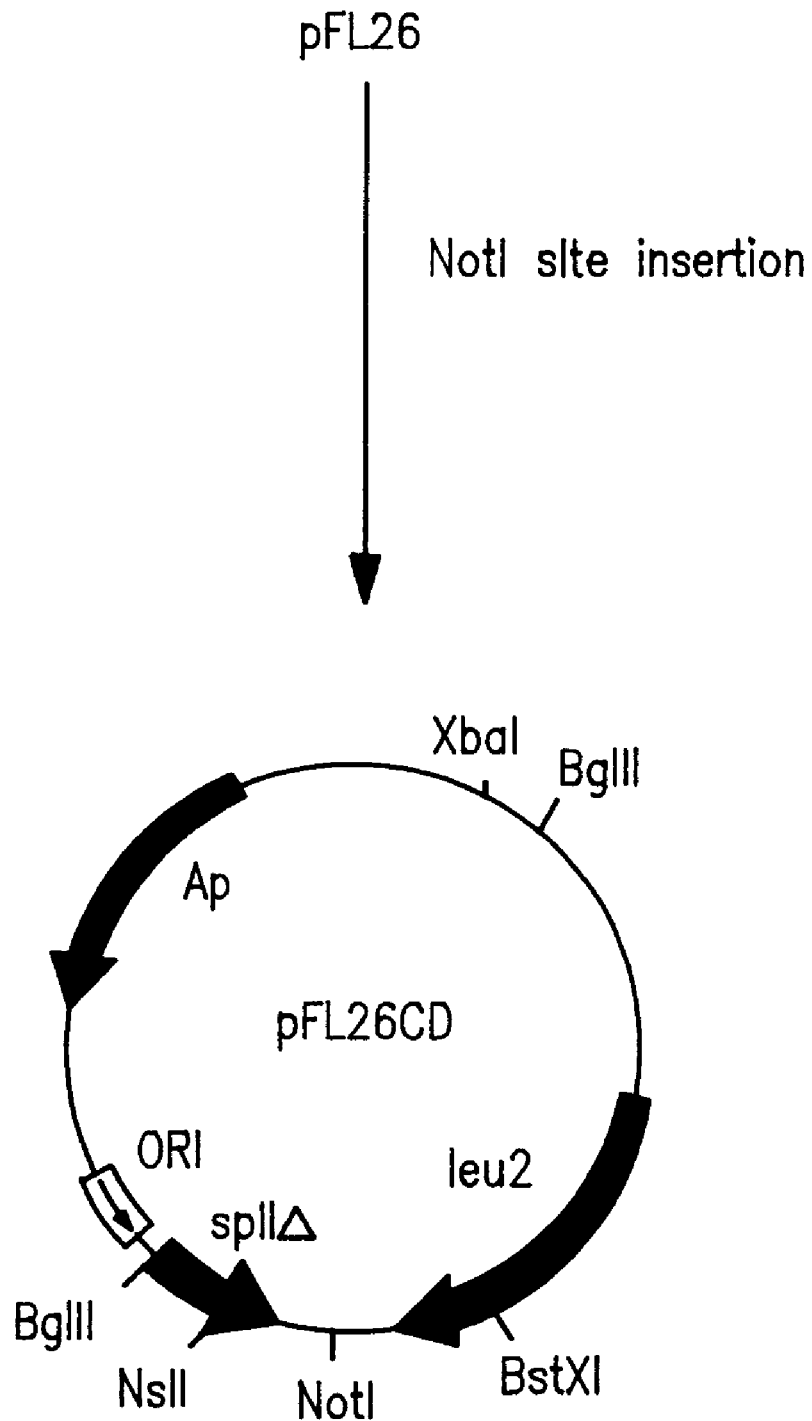
Figure 9B:
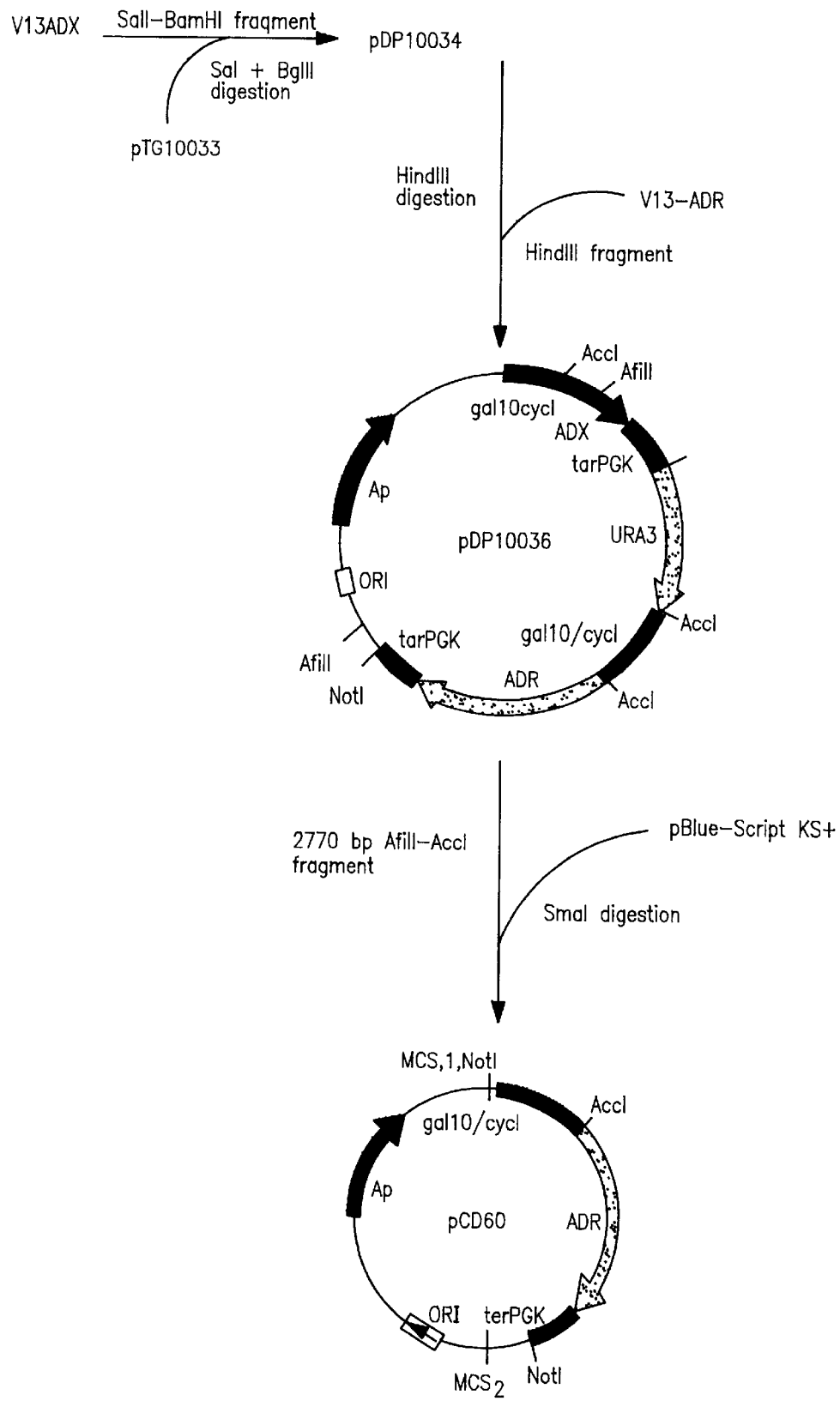
Figure 9C:
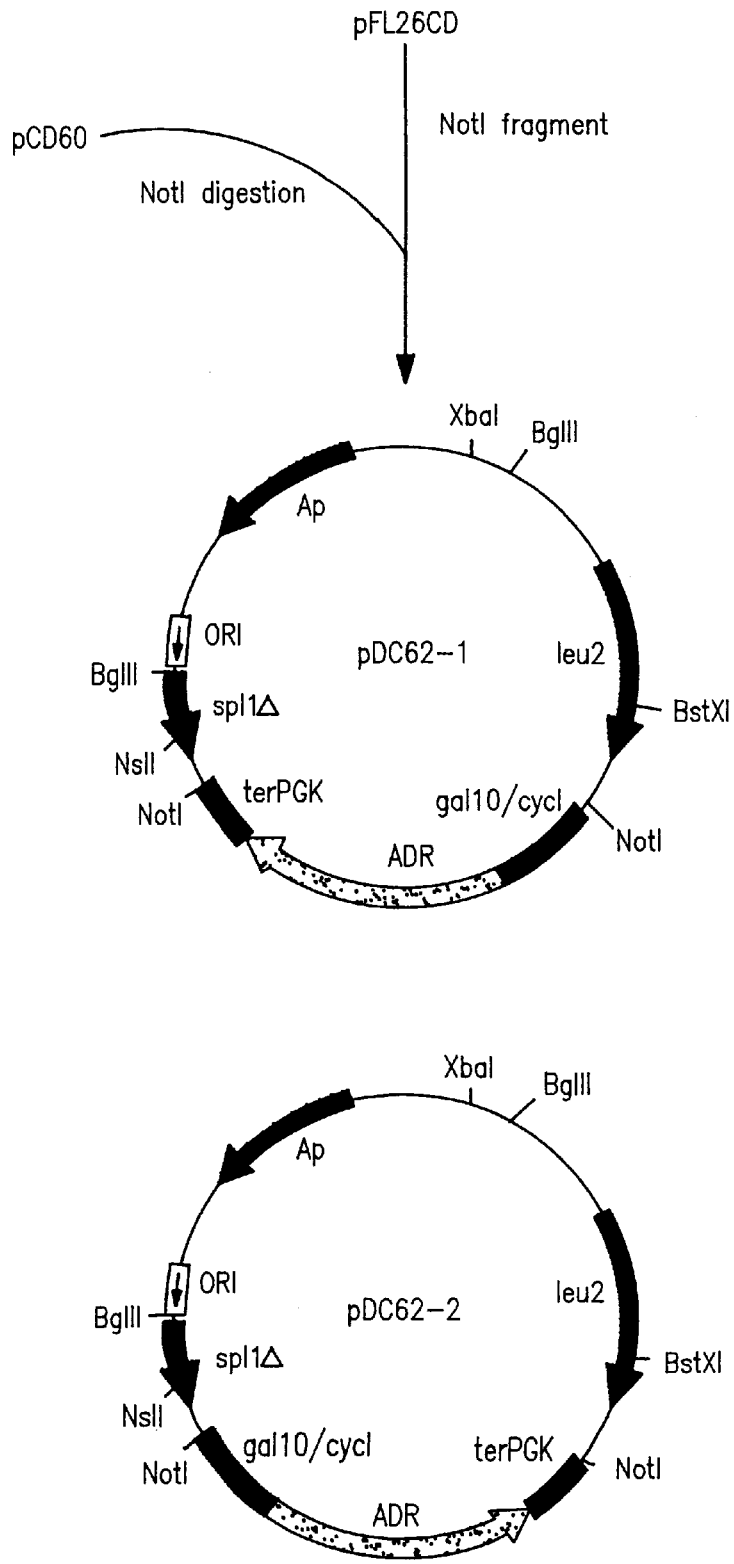

FIGS. 9a, 9b and 9c represent the stages of construction of the integrative plasmids pCD62-1 and pCD62-2 which allow the ADR expression cassette to be inserted in the intergenic region of genes leu2 and spl1Δ. MCS1 and MCS2: multiple cloning sites.

Figure 10:
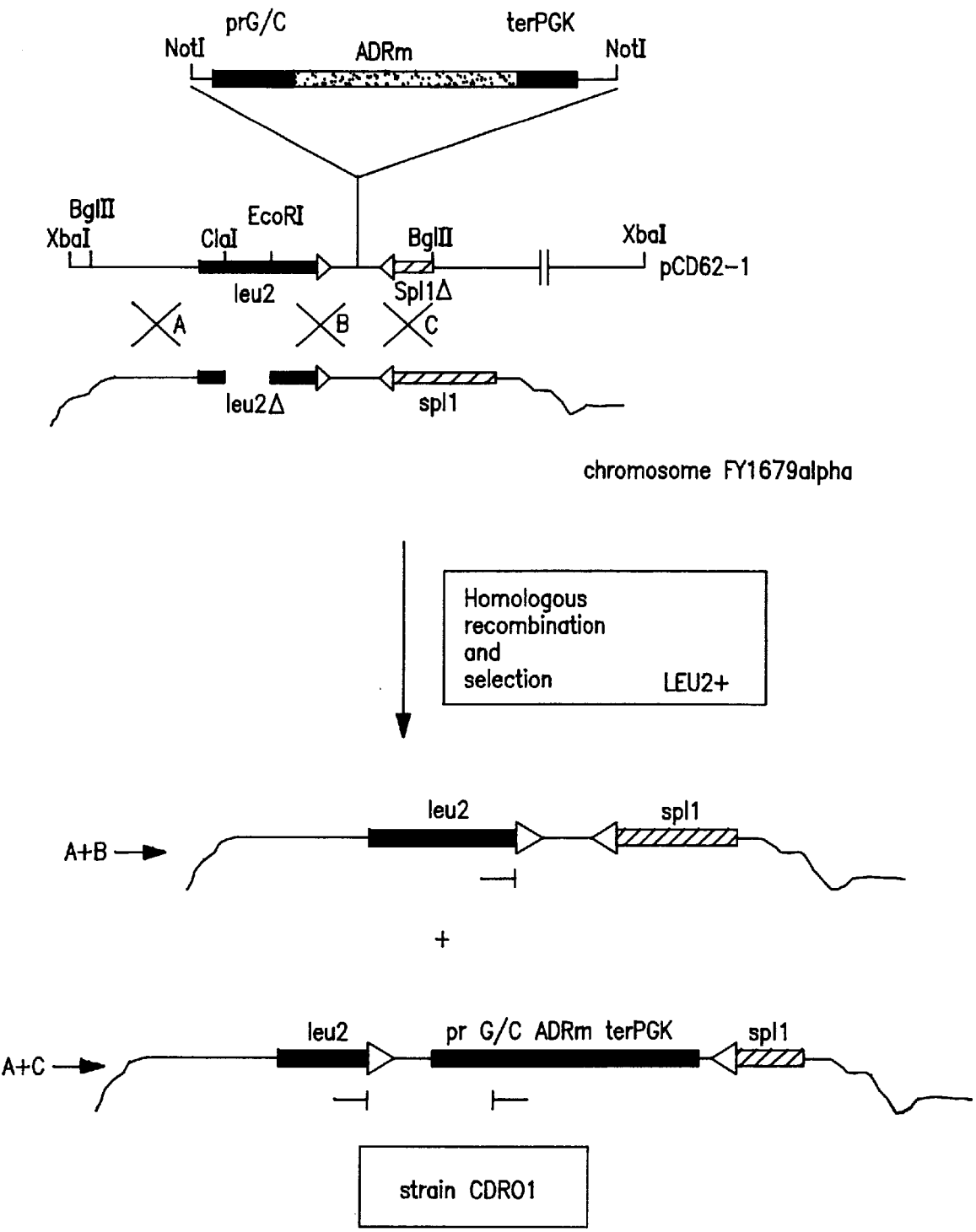

FIG. 10 represents the construction strategy of the strain CDR01.

Figure 11A:
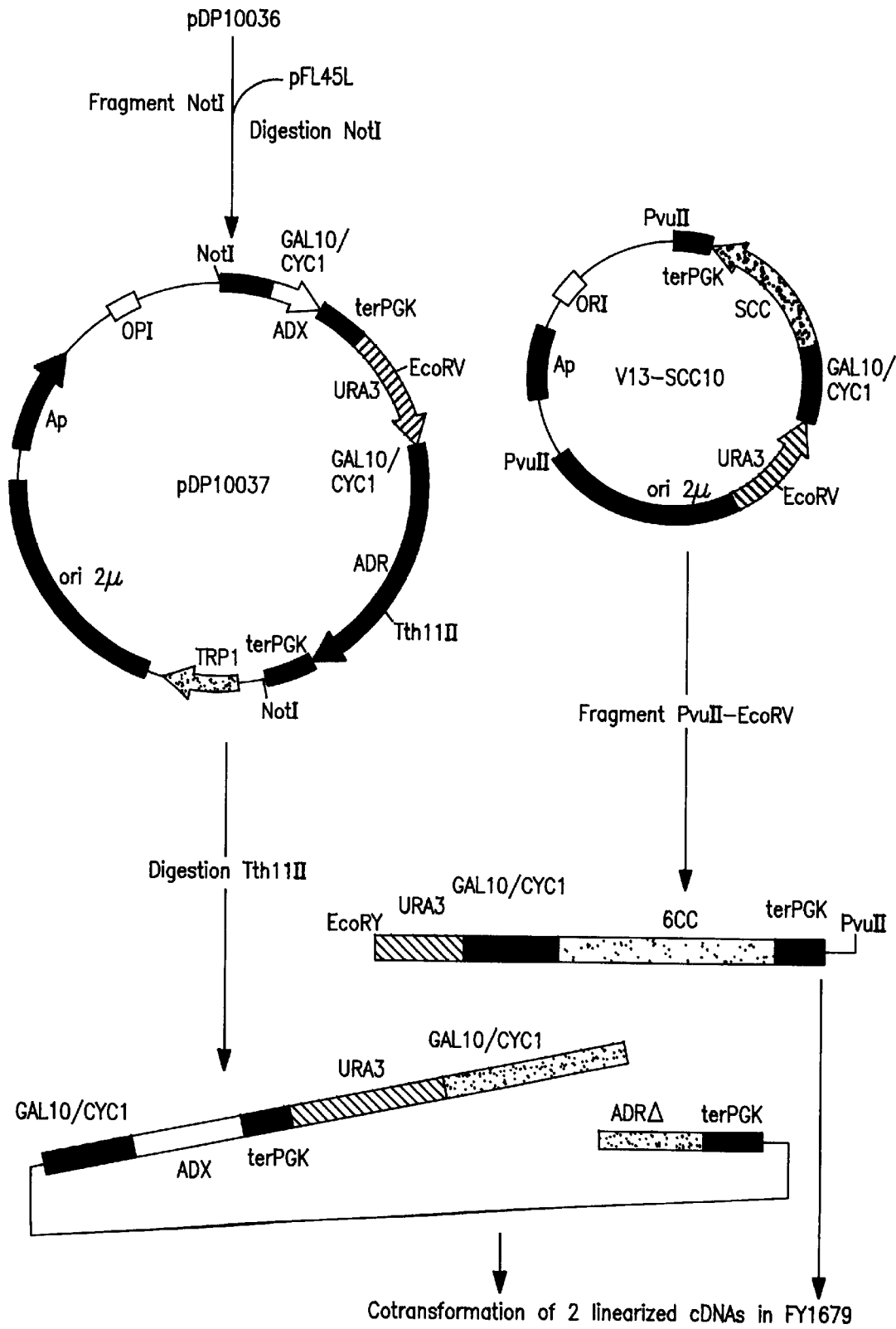

FIGS. 11a and 11b represent stages of construction of the expression plasmid pCD63 containing the two expression cassettes ADX and $P_{450}SCC$.

Figure 12A:
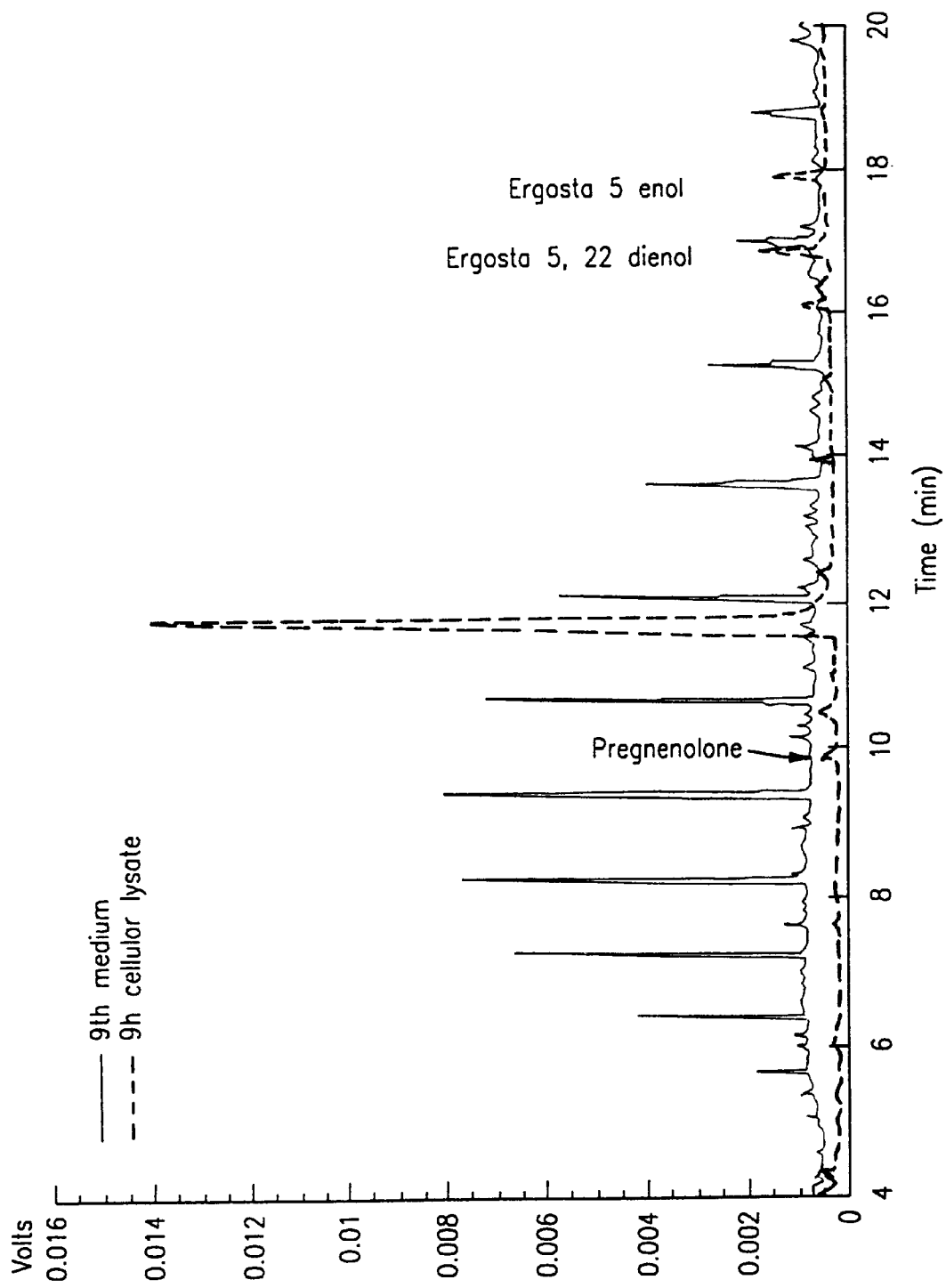
Figure 12B:
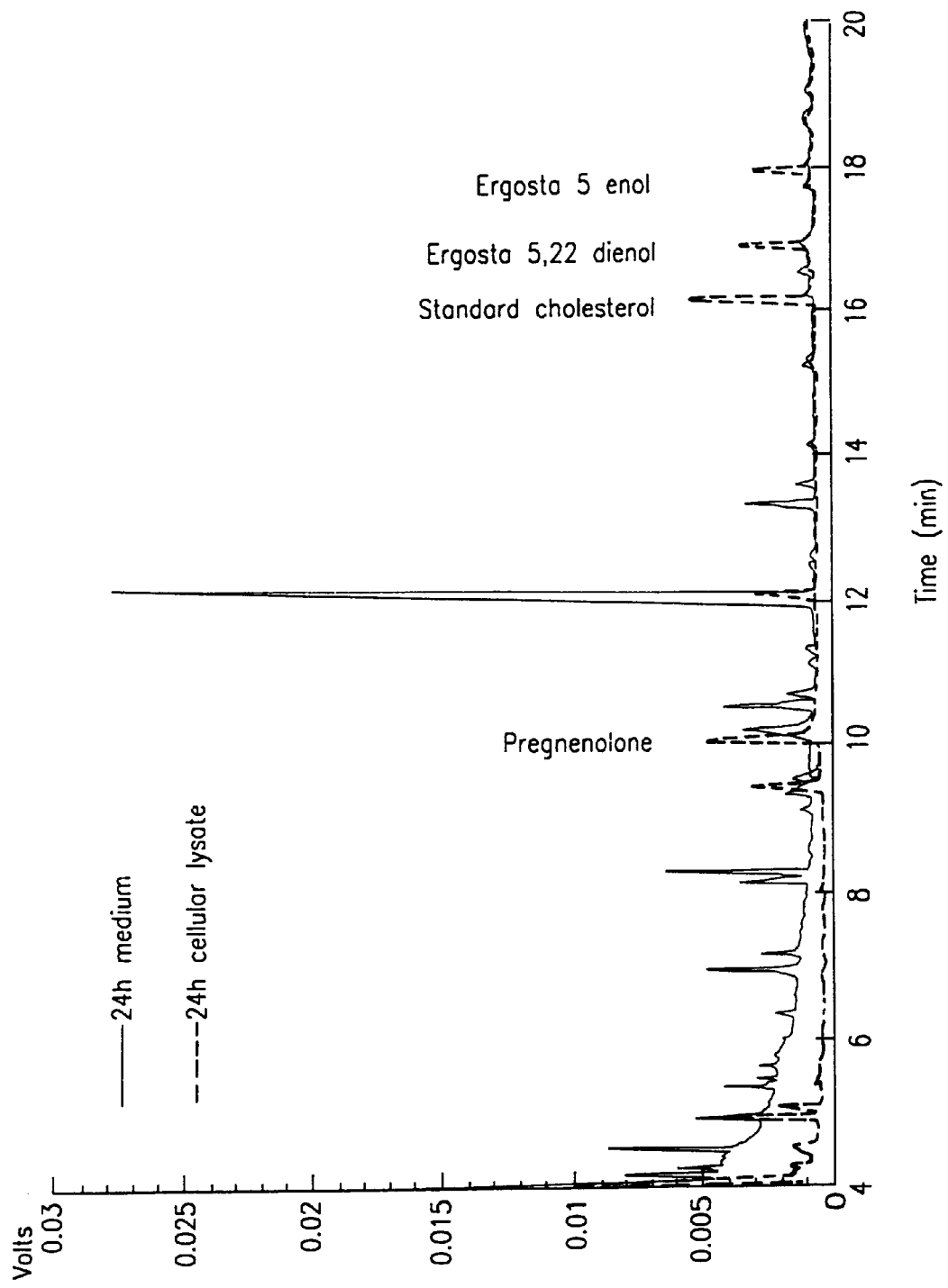

FIGS. 12a and 12b are graphs of the analysis by GC of the sterols extracted from cells (cellular lysate) or culture medium (medium) isolated from the strain EC01/pCD63 after an induction by galactose for 9 hours (FIG. 12a) or 24 hours (FIG. 12b).

Figure 13:
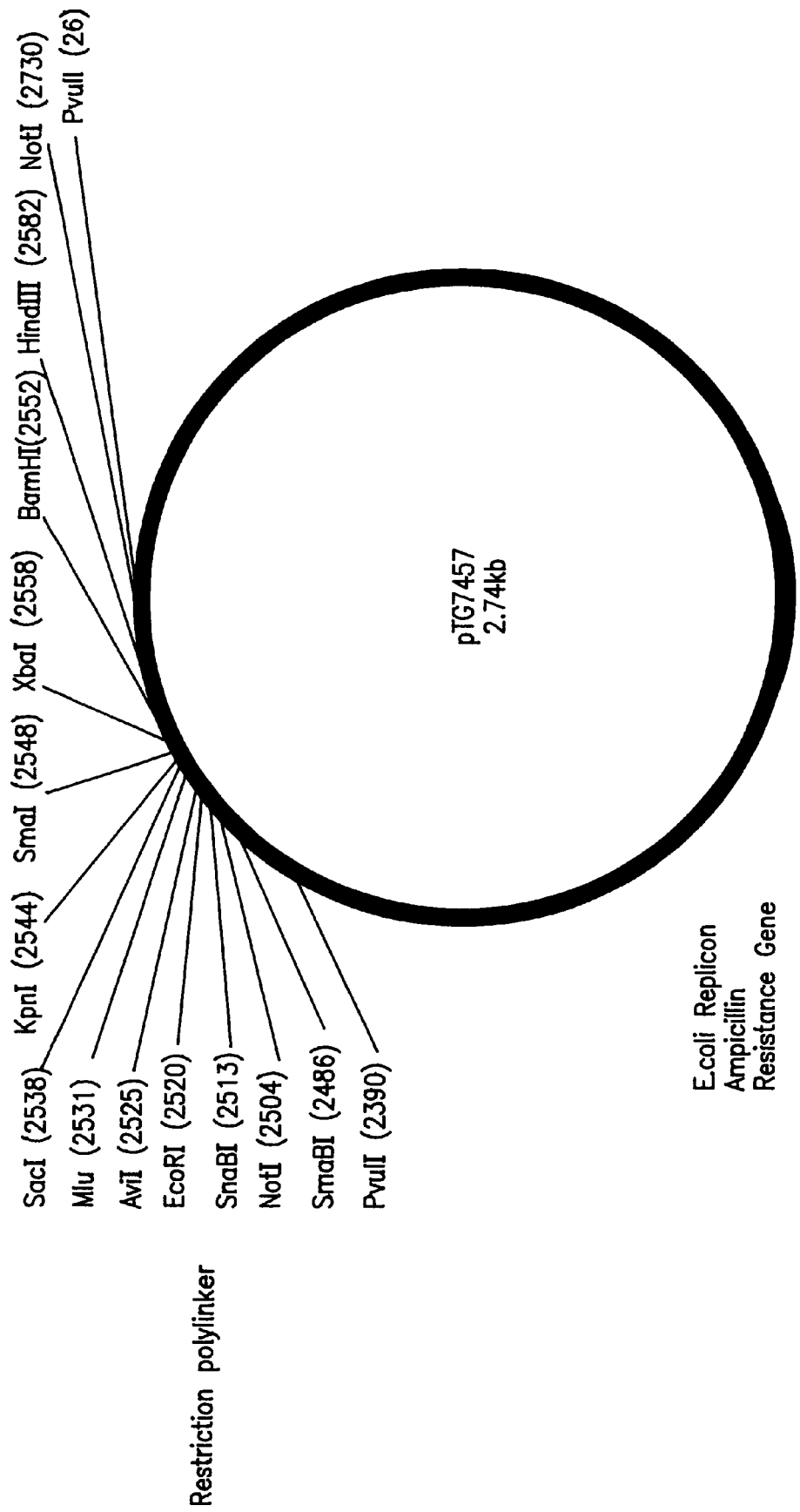

FIG. 13 represents the structure of plasmid pTG 7457.

Figure 14:
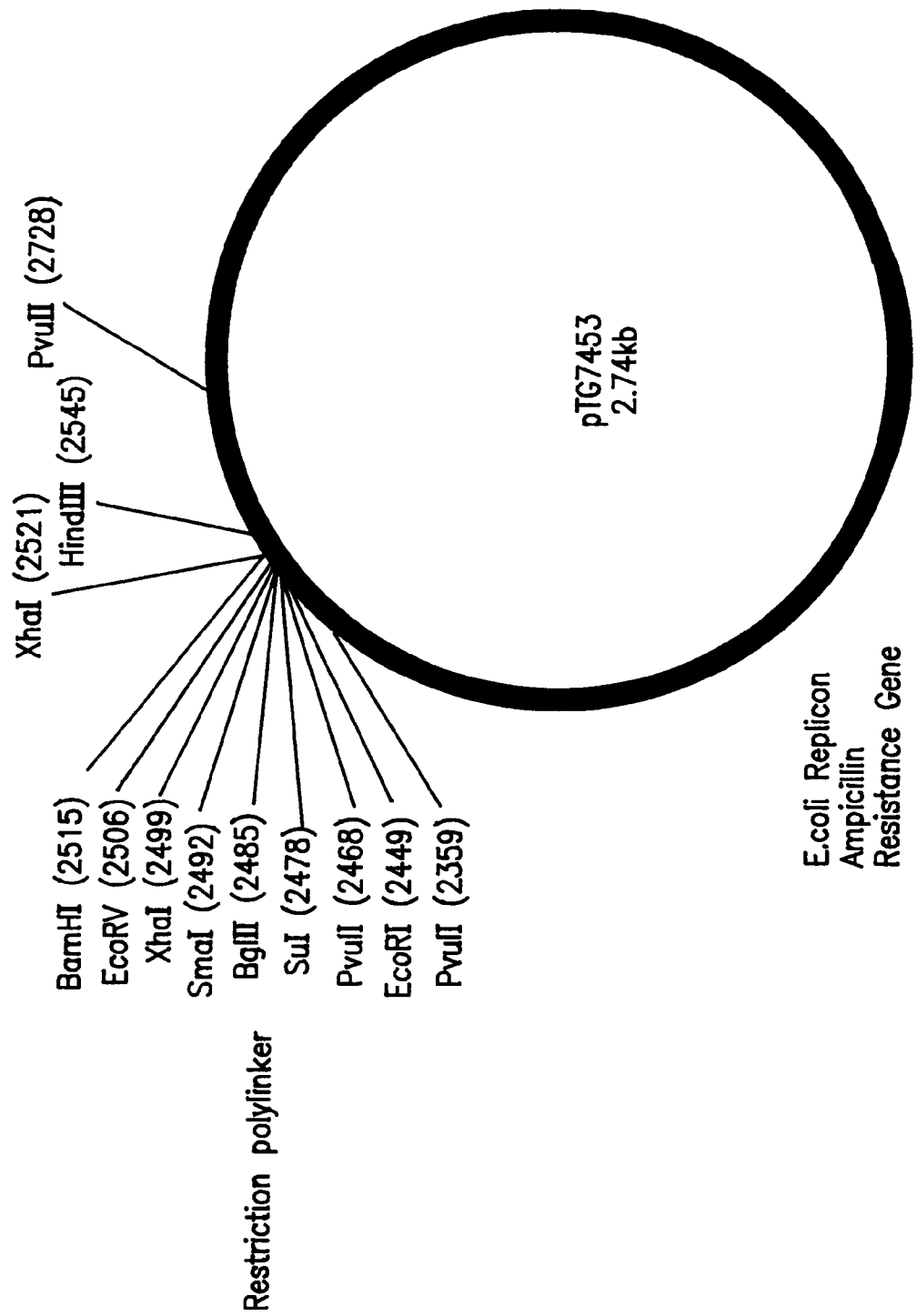

FIG. 14 represents the structure of plasmid pTG 7453.

Figure 15:
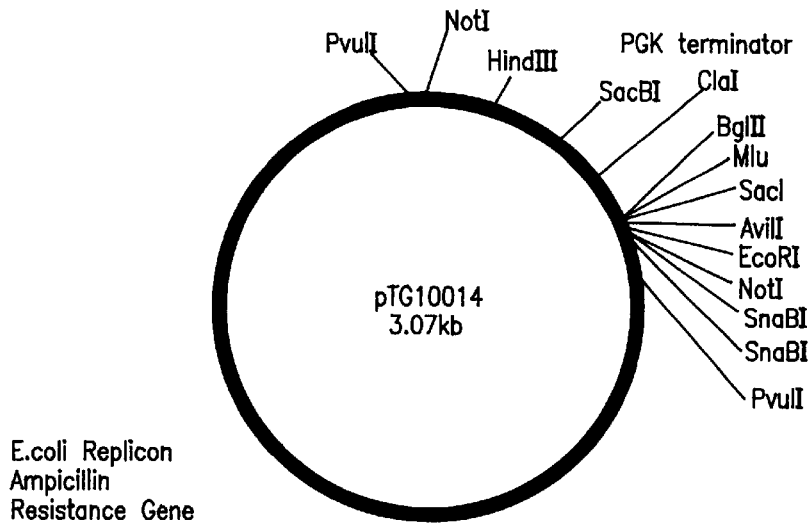

FIG. 15 represents the structure of plasmid pTG 10014.

Figure 16:
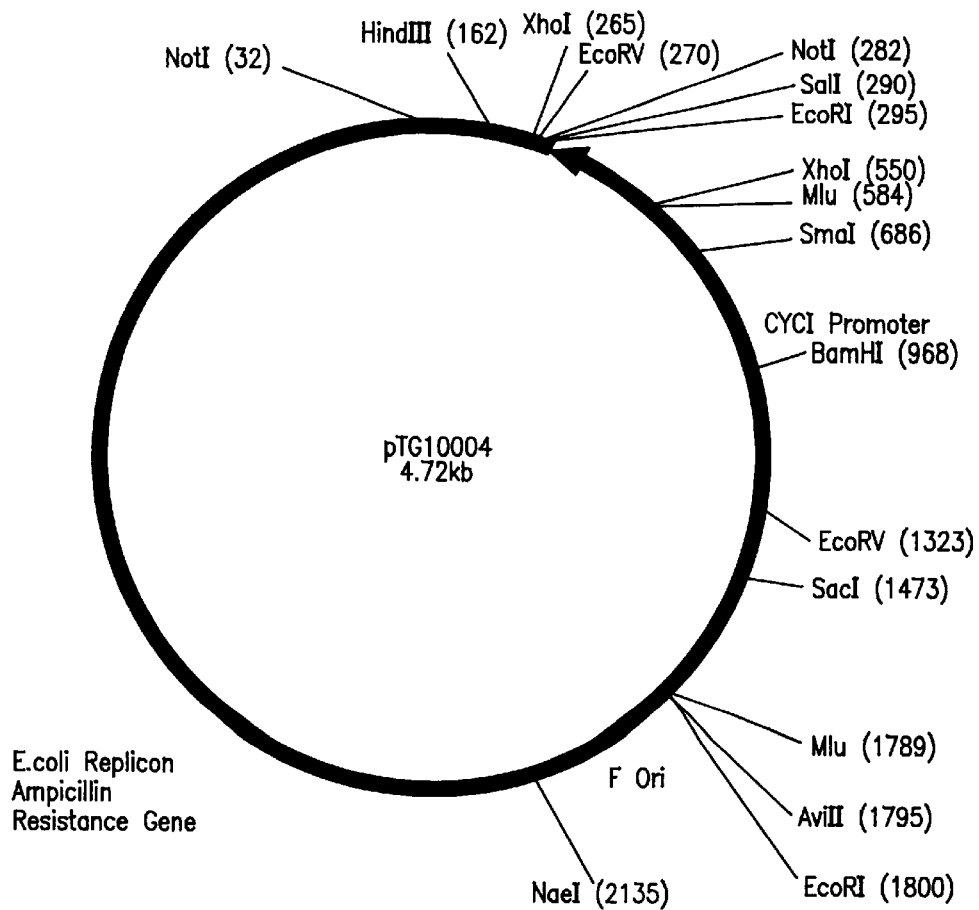

FIG. 16 represents the structure of plasmid pTG 10004.

Figure 17:
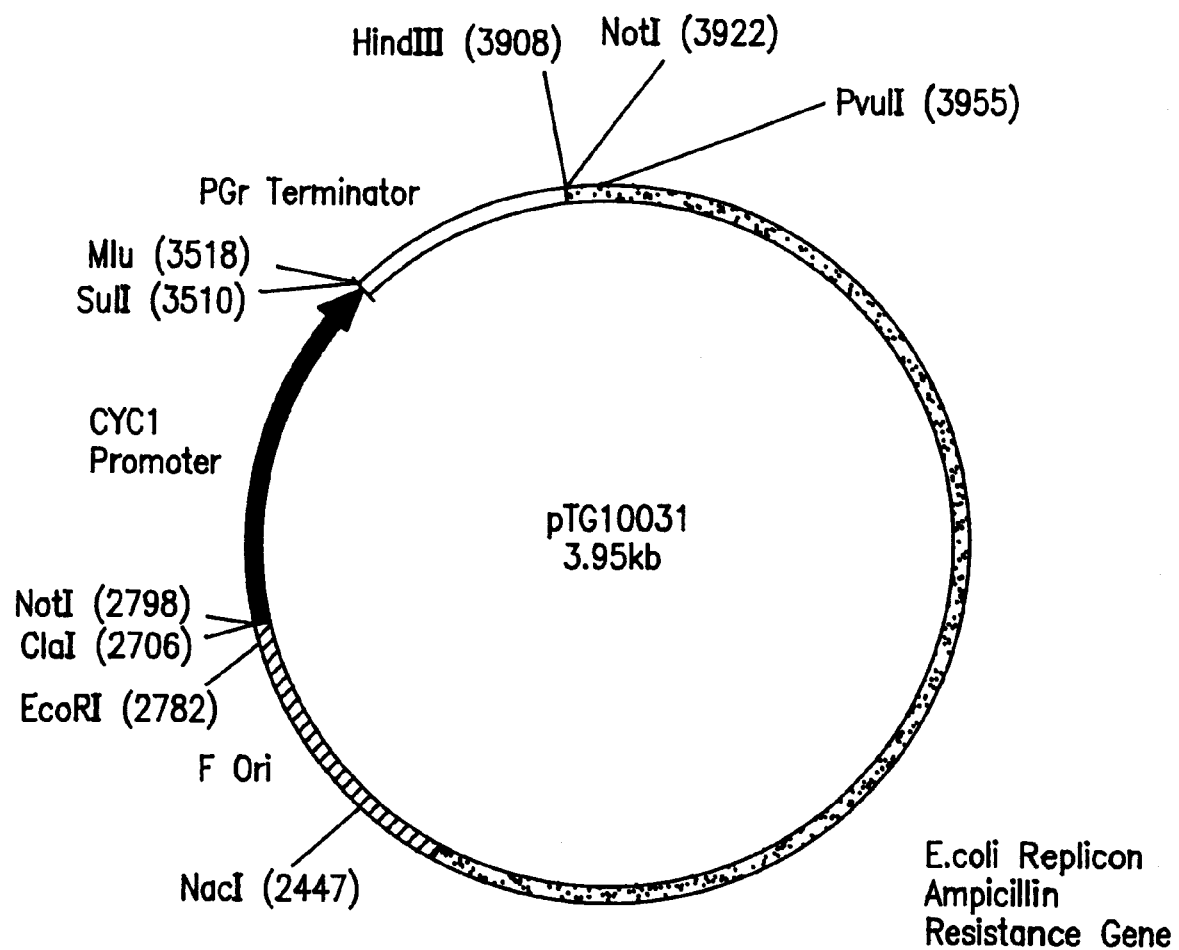

FIG. 17 represents the structure of plasmid pTG 10031.

Figure 18:
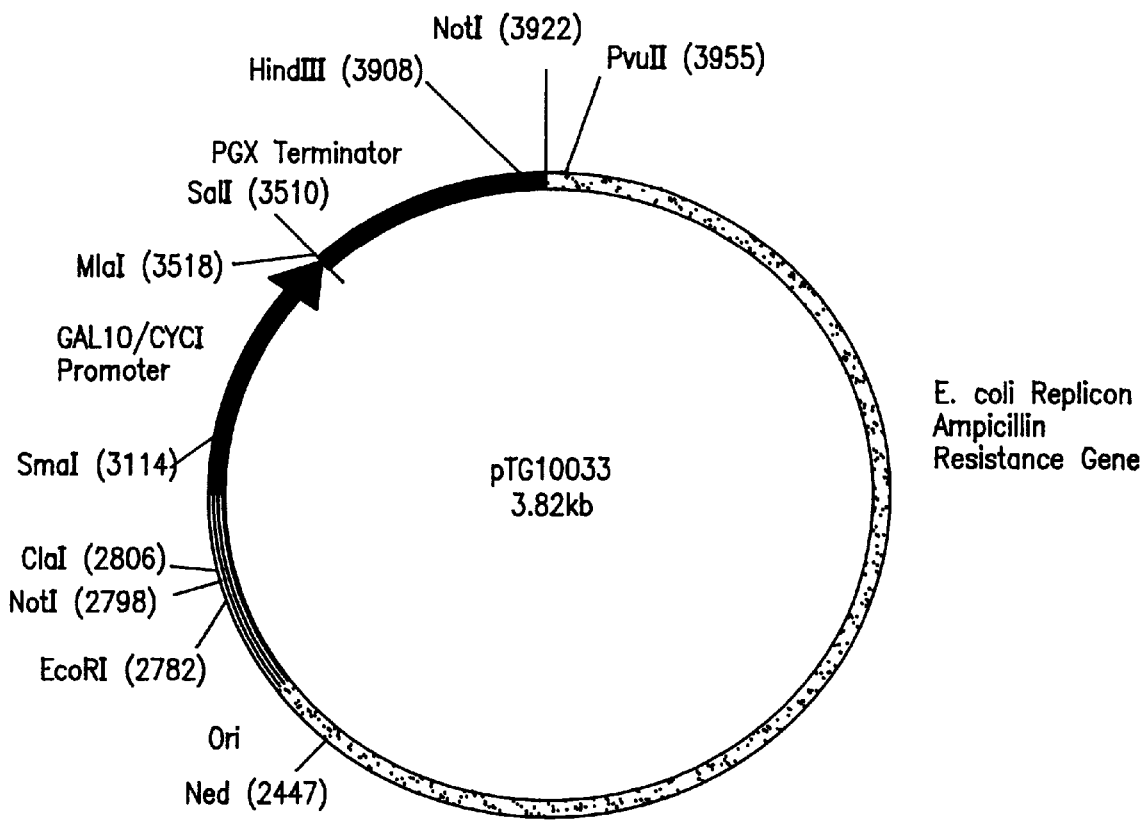

FIG. 18 represents the structure of plasmid pTG 10033.

Knowledge of the nucleotide sequence SEQ ID No. 1 above allows the invention to be reproduced by methods known to one skilled in the art, for example by chemical synthesis or by screening a gene library or a cDNA library using synthetic oligonucleotide probes by hybridization techniques or by PCR amplification.

Also an object of the invention is a DNA sequence coding for a protein having a delta-5,7 sterol, delta-7 reductase activity and which hybridizes with the nucleotide sequence SEQ ID No. 1 under conditions of average or high stringency or which have a sequence identity of approximately 60% and more with this sequence.

The sequences which hybridize in a detectable manner with sequence SEQ ID No. 1 hybridize under standard conditions of average stringency, for example a hybridization at 42° C. for 12 hours in a 50% solution of formamide, SSCX6 followed by washings or under less stringent conditions, for example a hybridization at 42° C. for 24 hours in a 20% solution of formamide, SSCX6 followed by washings under known standard conditions (Maniatis et al., Molecular cloning, Cold Spring Harbor Laboratory Press, 1989).

The percentage of nucleotide sequence identity can be determined by using for example the BLAST program "basic local alignment search tool" (Altschul et al., J. Mol. Biol., Vol. 215, pp. 403–410, 1990) on the NCBI server.

The invention also relates to a DNA sequence coding for a protein having a delta-5,7 sterol, delta-7 reductase activity and amplifiable by the PCR technique using as primers, the oligo-nucleotides coding for a consensus sequence having the amino acid sequence SEQ ID No. 3:

```
Leu Leu Xaa Xaa Gly Trp Xaa Gly Xaa Xaa Arg Xaa Xaa Xaa Tyr
1               5                  10                  15
``` in which Xaa in position 7 is Trp or Tyr and Xaa in position 12 is His or Lys.

The above sequence SEQ ID No. 3 corresponds to a new consensus sequence which has been defined by alignment of the identity of amino acid sequences between the new sequence SEQ ID No. 2, deduced from the nucleotide sequence SEQ ID No. 1, and known sequences either of other sterol reductases having a specificity of action at a position other than position C-7, or of lamin B receptors, as is detailed further on in the Examples. From the information given by the amino acid sequence SEQ ID No. 3, a primer constituted by at most 45 nucleotides can be defined and synthesized which, combined with a second primer oligodT (17 nucleotides) as rebound sequence, will allow using a commercially-available PCR assay kit (for example Stratagene) the amplification of a DNA coding for a protein having delta-5,7 sterol, delta-7 reductase activity.

The invention also relates to a protein of A. thaliana having a delta-5,7 sterol, delta-7 reductase activity and having the amino acid sequence SEQ ID No. 2:

```
Met Ala Glu Thr Val His Ser Pro Ile Val Thr Tyr Ala Ser Met Leu
 1               5                  10                  15

Ser Leu Leu Ala Phe Cys Pro Pro Phe Val Ile Leu Leu Trp Tyr Thr
            20                  25                  30

Met Val His Gln Asp Gly Ser Val Thr Gln Thr Phe Gly Phe Phe Trp
        35                  40                  45

Glu Asn Gly Val Gln Gly Leu Ile Asn Ile Trp Pro Arg Pro Thr Leu
    50                  55                  60

Ile Ala Trp Lys Ile Ile Phe Cys Tyr Gly Ala Phe Glu Ala Ile Leu
65                  70                  75                  80

Gln Leu Leu Leu Pro Gly Lys Arg Val Glu Gly Pro Ile Ser Pro Ala
                85                  90                  95

Gly Asn Arg Pro Val Tyr Lys Ala Asn Gly Leu Ala Ala Tyr Phe Val
            100                 105                 110

Thr Leu Ala Thr His Leu Gly Leu Trp Trp Phe Gly Ile Phe Asn Pro
        115                 120                 125

Ala Ile Val Tyr Asp His Leu Gly Glu Ile Phe Ser Ala Leu Ile Phe
    130                 135                 140

Gly Ser Phe Ile Phe Cys Val Leu Leu Tyr Ile Lys Gly His Val Ala
145                 150                 155                 160

Pro Ser Ser Ser Asp Ser Gly Ser Cys Gly Asn Leu Ile Ile Asp Phe
                165                 170                 175

Tyr Trp Gly Met Glu Leu Tyr Pro Arg Ile Gly Lys Ser Phe Asp Ile
            180                 185                 190

Lys Val Phe Thr Asn Cys Arg Phe Gly Met Met Ser Trp Ala Val Leu
        195                 200                 205

Ala Val Thr Tyr Cys Ile Lys Gln Tyr Glu Ile Asn Gly Lys Val Ser
    210                 215                 220

Asp Ser Met Leu Val Asn Thr Ile Leu Met Leu Val Tyr Val Thr Lys
225                 230                 235                 240

Phe Phe Trp Trp Glu Ala Gly Tyr Trp Asn Thr Met Asp Ile Ala His
                245                 250                 255

Asp Arg Ala Gly Phe Tyr Ile Cys Trp Gly Cys Leu Val Trp Val Pro
            260                 265                 270

Ser Val Tyr Thr Ser Pro Gly Met Tyr Leu Val Asn His Pro Val Glu
        275                 280                 285

Leu Gly Thr Gln Leu Ala Ile Tyr Ile Leu Val Ala Gly Ile Leu Cys
    290                 295                 300

Ile Tyr Ile Lys Tyr Asp Cys Asp Arg Gln Arg Gln Glu Phe Arg Arg
305                 310                 315                 320

Thr Asn Gly Lys Cys Leu Val Trp Gly Arg Ala Pro Ser Lys Ile Val
                325                 330                 335

Ala Ser Tyr Thr Thr Thr Ser Gly Glu Thr Lys Thr Ser Leu Leu Leu
            340                 345                 350

Thr Ser Gly Trp Trp Gly Leu Ala Arg His Phe His Tyr Val Pro Glu
        355                 360                 365

Ile Leu Ser Ala Phe Phe Trp Thr Val Pro Ala Leu Phe Asp Asn1 Phe
    370                 375                 380

Leu Ala Tyr Phe Tyr Val Leu Thr Leu Leu Phe Asp Arg Ala Lys
385                 390                 395                 400

Arg Asp Asp Asp Arg Cys Arg Ser Lys Tyr Gly Lys Tyr Trp Lys Leu
            405                 410                 415

Tyr Cys Glu Lys Val Lys Tyr Arg Ile Ile Pro Gly Ile Tyr
        420                 425                 430
``` as well as the allelic variants and analogues of this sequence.

By alleles and analogs, are included sequences modified by substitution, deletion or addition of one or more amino acids as long as these products retain the same function. The modified sequences can be, for example, prepared by using the site directed mutagenesis technique known to one skilled in the art.

A particular object of the invention is a protein of *A. thaliana* having a delta-5,7 sterol, delta-7 reductase activity and having the amino acid sequence SEQ ID No. 2 above and designated delta-7Red. The invention also relates to a protein having a delta-5,7 sterol, delta-7 reductase activity having an amino acid sequence with an identity of sequence of approximately 60% and more with the sequence SEQ ID No. 2. The percentage of identity can be determined for example by using the BLAST program indicated above.

The invention also relates to a protein having a delta-5,7 sterol, delta-7 reductase activity and having a crossed immunological reactivity with the protein of *A. thaliana* delta-7Red defined above. The protein can be detected, for example, by immuno-precipitation using an anti-serum directed against the delta-7Red protein, prepared by known methods.

One of the aspects of the invention relates to a protein having a delta 5,-7 sterol, delta-7 reductase activity such as that obtained by expression in a host cell containing a DNA sequence defined previously and particularly relates to a protein of *A. thaliana* such as that obtained by expression in a host cell containing a DNA sequence coding for the amino acid sequence SEQ ID No. 2 above.

When the protein of the invention is obtained by expression in a host cell, this is carried out by genetic engineering and cell culture methods known to one skilled in the art. Expression can be carried out in a procaryotic host cell, for example *E. coli* or in a eucaryotic host cell, for example a mammalian cell, an insect cell or a yeast containing the sequence coding for delta-7 Red of the invention preceded by a suitable promoter. The recombinant protein obtained can be glycosylated or non-glycosylated.

In particular, the invention relates to a protein of the invention such as that obtained by expression in a yeast.

The invention also relates to an antibody directed against a protein having a delta-5,7 sterol, delta-7 reductase activity defined previously. The antibody can be a polyclonal antibody or a monoclonal antibody prepared by methods known to one skilled in the art.

The invention also relates to an expression vector containing a DNA sequence defined previously as well as to a host cell transformed by this vector. The expression vectors are known vectors allowing the expression of the protein under the control of a suitable promoter. For the procaryotic cells, the promoter can be, for example, the lac promoter, the trp promoter, the tac promoter, the β-lactamase promoter or the PL promoter. For mammalian cells, the promoter can be the SV40 promoter or the promoters of the adeno-virus. Vectors of Baculovirus type can also be used for expression in insect cells For yeast cells, the promoter can be for example the PGK promoter, the ADH promoter, the CYC1 promoter or the GAL10/CYC1 promoter.

The host cells can be procaryotic cells or eucaryotic cells. Procaryotic cells are, for example, *E. coli*, Bacillus or Streptomyces. Eucaryotic host cells include yeasts and filamentous fungi as well as cells of higher organisms, for example, cells of mammals or cells of insects. The mammalian cells can be hamster CHO cells or monkey Cos cells and the insect cells are, for example, SF9 cells. The yeast cells can be, for example, *Saccharomyces cerevisiae, Schizosaccharomyces pombe* or *Kluyveromyces lactis*.

Also an object of the invention is a cloning process for a nucleic acid coding for a protein having a delta-5,7 sterol, delta-7 reductase activity in a microorganism comprising a screening method chosen from

- the resistance of the microorganism to nystatin or to an analogous compound whose toxicity depends on the presence of sterols carrying an unsaturation in position C-7,
- the hybridization of the nucleic acid with the nucleotide sequence of the sequence SEQ ID No. 1 above,
- the identification of the nucleic acid by using data processing techniques from DNA sequences isolated at random, or
- the direct expression of the protein followed by immuno-detection using antibodies directed against the protein having the amino acid sequence SEQ ID No. 2 above.

By microorganism is meant a yeast such as *S. cerevisiae, S. pombe* or *K. lactis*. The compounds analogous to nystatin include for example amphotericin B or filipin. By hybridization is meant a hybridization under average or high stringency conditions by known standard conditions (Maniatis et al., already quoted).

Identification using data-processing techniques can be carried out for example according to the BLAST program indicated above. An example of the above cloning process in which the screening method uses the resistance to nystatin in a yeast is described further on in the Examples.

Another object of the invention is a DNA or RNA nucleic acid sequence, as obtained by the above cloning process. The nucleic acid sequence can be of procaryotic or eucaryotic origin depending on the material from which the cloning is carried out, for example of human origin.

A further object of the invention is a host cell transformed by a vector containing a DNA sequence as obtained by the above cloning process. The host cell can be a procaryotic cell or a eucaryotic cell. Examples of host cells and vectors have been indicated previously. A particular object of the invention is a host cell, chosen from a yeast or a filamentous fungus, transformed by a vector containing a DNA sequence of invention defined previously or a DNA sequence such as that obtained by the above cloning process.

One of the objects of the invention relates to a preparation process for a protein having a delta-5,7 sterol, delta-7 reductase activity in which a transformed host cell of the invention is cultivated and the expressed protein is isolated and particularly relates to a process in which the host cell is a transformed yeast in which the coding DNA sequence is placed under the control of a yeast promoter.

An additional object of the invention relates to a reduction process in vitro of a sterol unsaturated in position C-7 in which the sterol to be reduced is incubated with the protein obtained by the above process and the reduced sterol obtained is optionally isolated. The invention also relates to a reduction process in vivo of an exogenic sterol unsaturated in position C-7 in which the sterol is incubated with a transformed host cell of the invention and the reduced sterol obtained is optionally isolated. The host cell can be a procaryotic cell or a eucaryotic cell, in particular a yeast or a filamentous fungus.

The invention also relates to a reduction process in vivo of an endogenic sterol unsaturated in position C-7 in which a transformed host strain of the invention chosen from a yeast or a filamentous fungus is cultivated and the accumulated reduced sterol is optionally isolated.

In particular, the invention relates to a reduction process in vitro or in vivo defined above in which the reduced sterol obtained is a substrate of the cleavage enzyme of the side chain of cholesterol ($P_{450}SCC$) and more preferably relates to a reduction process in vivo in which the endogenic sterol to be reduced is ergosta 5,7 diene 3-ol, ergosta 5,7,24(28) triene 3-ol or ergosta 5,7,22 triene 3-ol or a mixture of these.

The invention also relates to a production process for pregnenolone in which a transformed host cell of the invention chosen from a yeast or a filamentous fungus is cultured, the accumulated endogenic sterol or sterols reduced in position C-7 are optionally isolated, the reduced sterols are incubated in the presence of $P_{450}SCC$ and optionally in the presence of adrenodoxin reductase (ADR) and adrenodoxin (ADX), and the pregnenolone obtained is optionally isolated. Preferably, the host cell is a yeast.

The invention also relates to a production process for pregnenolone in which a yeast transformed by one or more vectors allowing the coexpression of a protein having the activity of delta-5,7 sterol, delta-7 reductase and $P_{450}SCC$ and optionally of ADR and ADX is cultured and the free or esterified pregnenolone is optionally isolated. Preferably, the transformed yeast coexpressing a protein having the activity of delta-5,7 sterol delta-7 reductase, P450SCC, ADR and ADX are cultured, quite particularly the above process in which the protein having the delta-5,7 sterol delta-7 reductase activity is the protein of A. thaliana delta-7Red and especially the yeast strain is the strain EC01/pCD63. Examples of the production of pregnenolone of the invention are given further on in the Examples.

The transformed yeast used for carrying out the production process for pregnenolone can be for example a yeast co-transformed by an expression vector of the invention containing a DNA sequence coding for a protein having a delta-5,7 sterol, delta-7 reductase activity and an expression vector of the cytochrome $P_{450}SCC$ and optionally of ADX and ADR. The expression vectors of the cytochrome $P_{450}SCC$ and/or ADX are known and preparations are described in European Patent Application EP 0340878 as well as further on in the Examples.

The transformed yeast used can also be a yeast in which the DNA sequence coding for the protein having delta-5,7 sterol, delta-7 reductase activity is integrated in a particular locus of the genome, for example at locus ADE2 and in which the ergosterol is no longer the majority sterol under the expression conditions of delta-7 reductase. The "integrated" yeast obtained can then be transformed by integrative expression cassettes or by expression vectors containing a DNA sequence coding for the cytochrome $P_{450}SCC$ and optionally for ADX and ADR. An example of the construction of yeast strains producing pregnenolone or its acetic ester in vivo is given in the Examples.

Therefore, an object of the invention is a transformed yeast strain coexpressing a protein having the activity of delta-5,7 sterol, delta-7 reductase, $P_{450}SCC$, ADR and ADX and accumulating free or esterified pregnenolone, preferably an above yeast strain in which the protein having the activity of delta-5,7 sterol, delta-7 reductase is the protein of A. thaliana delta-7Red and more preferably, a yeast strain called EC01/pCD63, the precise construction of which is given in the Examples.

The invention also extends to a human DNA sequence as obtained by the cloning process defined above used as a probe to diagnose a congenital deficiency in delta-5,7 sterol, delta-7 reductase. The deficiency in delta-5,7 sterol, delta-7 reductase includes for example the deficiency in 7-dehydrocholesterol reductase responsible for the abnormally low levels of cholesterol in the plasma.

The invention also relates to a detection method for the deficiency in delta-5,7 sterol, delta-7 reductase which includes the incubation of a sample containing human genomic DNA with the probe defined above under standard hybridization conditions and the revealing of the fixation or the absence of fixation of the probe to the genomic DNA, the absence of fixation or the reduction of the latter indicating a congenital deficiency in delta-5,7 sterol, delta-7 reductase. The method of the invention can permit detection of a congenital deficiency in prenatal delta-5,7 sterol, delta-7 reductase or in new-born babies as well as in patients suffering from various illnesses, particularly in patients having clinical manifestations of RSH/SLO syndrome.

In the following Examples, there are described several preferred embodiments to illustrate the invention. However, it is to be understood that the invention is not intended to be limited to the specific embodiments.

EXAMPLE 1

Cloning of the CDNA coding for delta-5,7 sterol, delta-7 reductase (delta-7Red) of A. thaliana A—Screening of the Expression Library of A. thaliana in Yeast The starting cDNA expression library was the library described by Minet et al. (Plant J., Vol. 2, pp. 417–422, 1992) which was prepared from mRNA of A. thaliana at the two-leaf germination stage and whose cDNA's bordered by the NotI site had been inserted at the Bst XI site of the expression cassette of the shuttle vector E. coli/S. cerevisiae pFL61. This cassette contains the promoter and terminator sequences of the phosphoglycerate kinase gene (PGK). The origin of replication of the yeast derived from the $2\mu$ sequence and a selection indicator URA3 ensured the propagation of the vector in the yeast. The propagation of the vector in E. coli was derived from the plasmid pUC19.

The yeast strain FY 1679 (Mata), which is an isogenic strain of the strain S288C described Thierry et al. (Yeast, Vol. 6, pp. 521–534, 1990), was transformed by the cDNA library using the lithium acetate method described by Gietz et al. (Nucleic Acids Res., Vol. 20, p. 1425, 1992).

The cells were plated on a synthetic medium SGI containing 7 g/l of "yeast nitrogen base" (Difco), 1 g/l of bactocasaminoacids (Difco), 20 g/l of glucose, 20 mg/l of tryptophan and which was free from uracil. $10^5$ prototrophic transformants for uracil were obtained, then grouped and again plated on the same synthetic medium free from uracil and containing 2 or 5 μg/ml of nystatin at the rate of $5\times 10^4$ cells per dish. $10^6$ cells for each nystatin concentration were screened in this way. After incubation for 3 days at 28° C., approximately 100 clones, which were grown at a concentration of 2 μg/ml of nystatin, were collected by constituting groups of 5 clones whose sterol composition was analyzed by reversed-phase high performance liquid chromatography (called RP-HPLC in what follows) while a single resistant clone, called F22, was obtained at a concentration of 5 μg/ml of nystatin.

B—Analysis of the Sterols Accumiulated in the Clone F22

The total sterols of the yeast were prepared according to the alkaline saponification method described by Parks et al. (Methods in Enzymol., Vol. 111, pp. 333–346, 1985), then analyzed by RP-HPLC and/or by gas chromatography (called GC).

The residue of sterols obtained was dissolved in an ethanol-tetrahydrofuran-water mixture (65:10:25 v/v), then analyzed by RP-HPLC on an Applied Biosystems C18 bonded silica column (100×2.1 mm) at a flow rate of 1 ml/min and at 55° C. using a linear gradient of methanol in water (50% to 100% over 18 min) and a photometric detection at 205 nm and 285 nm compared with the ergosterol, campesterol and cholesterol standards.

The composition of sterols was also analyzed by GC on an Alltech SE-30 capillary column (30 m×0.32 mm) with helium as carrier gas, a temperature of 280° C. and 310° C. for the injector and the detector respectively, with an initial increase in the temperature of 110° C. to 245° C. at a speed of 45° C./min, then of 3° C./min to reach 280° C.

The analysis by RP-HPLC (FIG. 1A) and the analysis by GC (FIG. 1B) show the profile of the accumulated sterols in the clone F22 obtained above characterized by the virtually complete disappearance of ergosterol, majority sterol of the non-transformed strain FY 1679, and its replacement by two majors sterols and in similar quantity which do not absorb at 285 nm and thus no longer have a conjugated double unsaturation according to analysis by RP-HPLC.

Figure 1A:
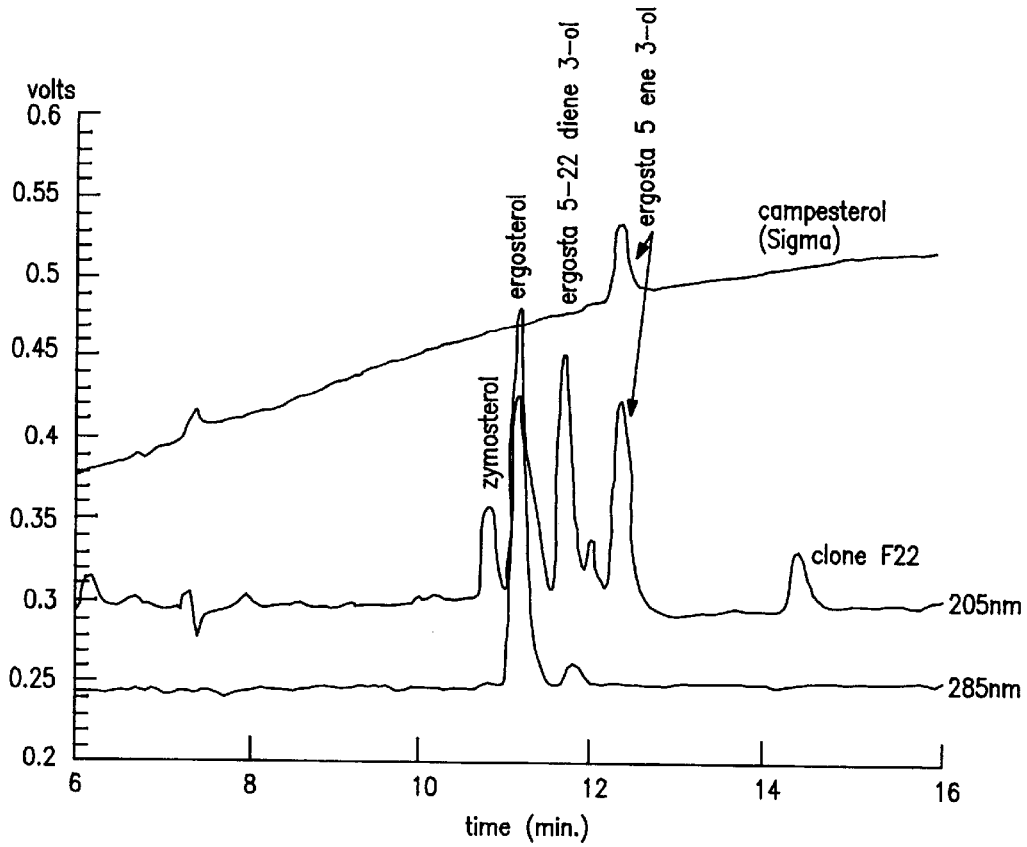
FIG. 1 is a graph of the profile in total sterols extracted from the clone F22 resistant to nystatin obtained by screening of the A. thaliana library in the yeast FY 1679. Analysis was carried out by RP-HPLC at 205 nm or at 285 nm (FIG. 1A) or by GC compared with the non-transformed yeast FY1679 (FIG. 1B).
Figure 1B:
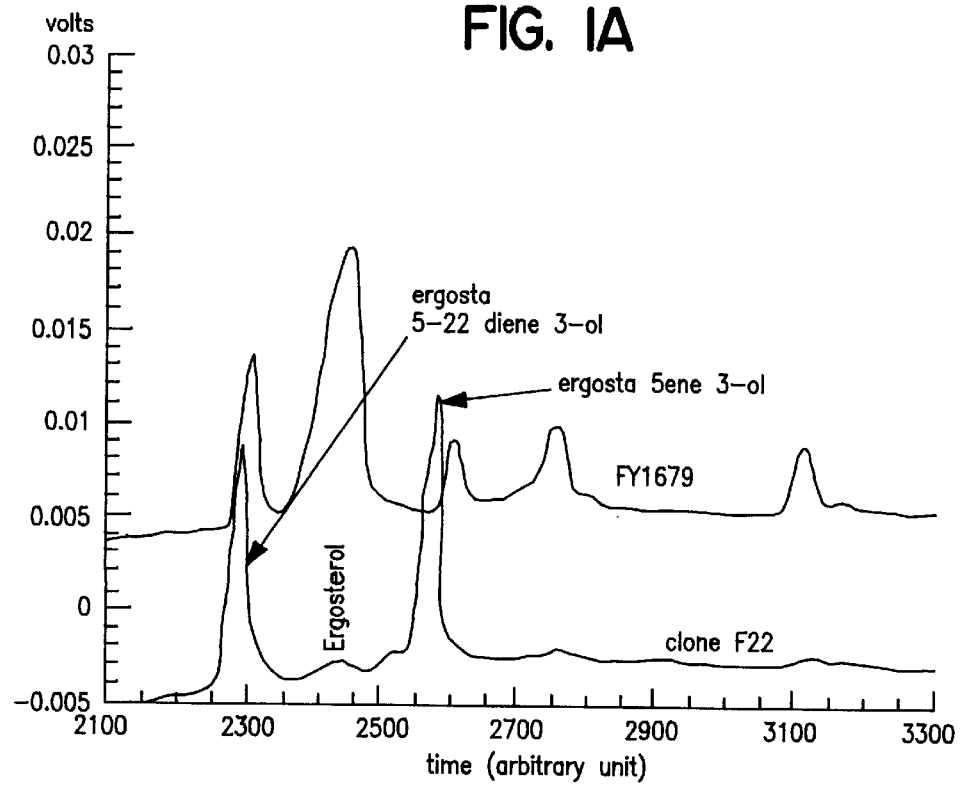

In FIG. 1A, the campesterol (Sigma) (24-R-ergosta 5-ene 3-ol) contains approximately 35% of dihydrobrassicasterol (24-S-ergosta 5-ene 3-ol).

C—Cloning of the delta-7Red cDNA

The plasmids originating from the clone F22 were amplified in $E.$ $coli$ according to the method described by Strathern et al. (Methods in Enzymol., Vol. 194, pp. 319–329, 1991), then digested by NotI. A fragment of about 600 base pairs (bp) and a fragment of 1.6 kbp were obtained. The strain FY1679 was transformed with each of the above fragments, respectively. The composition in sterols of each clone of the transformed yeast was analyzed as indicated above and allowed the plasmid carrying the gene responsible for the modified profile in sterols to be distinguished. The plasmid identified in this way was named pF22.

D—Determination of the cDNA Sequence of delta-7Red

Figure 2:
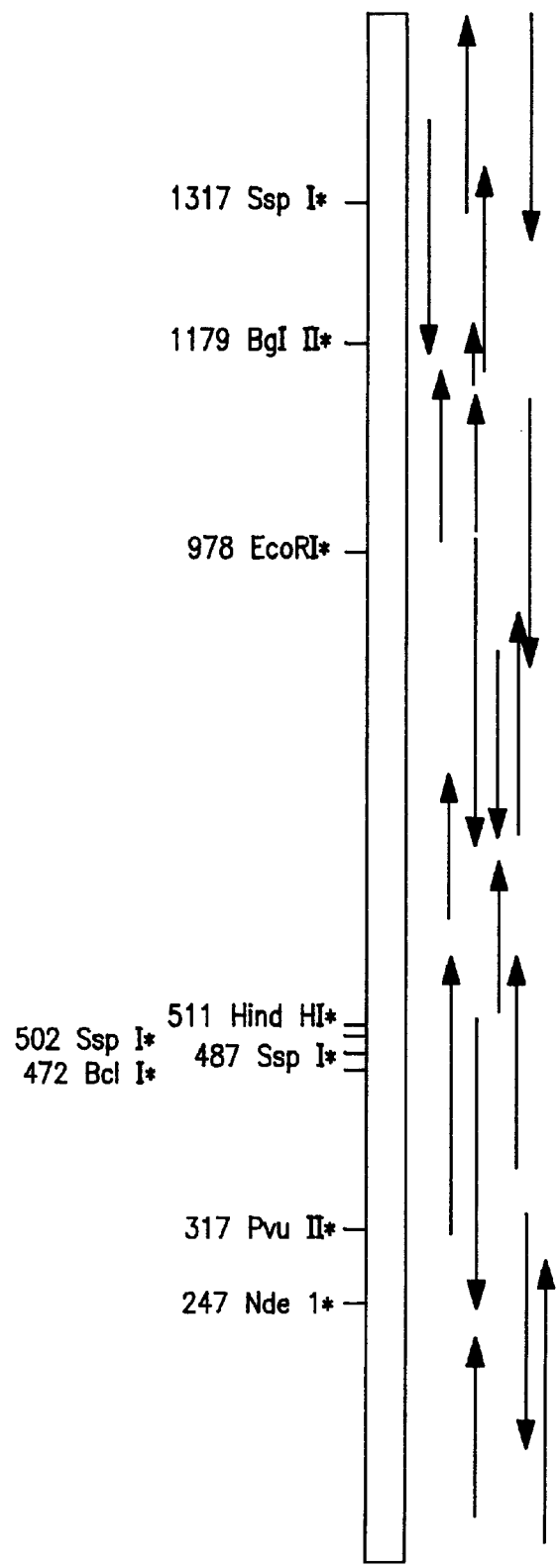
FIG. 2 is a restriction map of the NotI fragment of the plasmid pF22 and the sequencing strategy.

The cDNA insert of pF22 was sub-cloned at the NotI site of the vector pUC9N derived from pUC9 (Pharmacia) in which the Eco RI site of the multiple cloning site was replaced by the insertion of a NotI restriction site while retaining the reading frame of the LacZ gene. A restriction map was then determined (FIG. 2).

Restriction fragments having the NotI external site and the EcoRI, PvuII or HindIII internal sites respectively were sub-cloned in the pBluescript plasmid (Stratagene). The nucleotide sequence was determined by the Sanger method with DNA polymerase Sequenase (stratagene kit) on the two strands by using direct and inverse primers of pBluescript pUC9, T3 and T7 or deduced specific primers of the cDNA nucleotide sequence.

The compilation of all of the sequences obtained gave the delta-7Red cDNA nucleotide sequence of $A.$ $thaliana$ (SEQ ID No. 1) represented in FIG. 3. It comprised 1496 nucleotides ending with a polyadenylation sequence and it had an open reading frame starting with a methionine initiator at nucleotide 76 and ending with a termination codon at nucleotide 1366. This results in an open reading frame of 1290 nucleotides coding for a protein of 430 amino acids. The coding region of the delta-7Red cDNA codes for the protein delta-7Red the deduced amino acid sequence of which (SEQ ID No. 2) is shown in FIG. 3. The sequence of the protein included 430 amino acids amines having a calculated molecular mass of 49.286 kDa.

A sample of the $E.$ $coli$ DH5-1 strain containing delta-7Red cDNA in the vector pUC9N (designated delta7red/pUC9N cDNA) was deposited at the CNCM on Feb. 10th 1995 under the number I- 1535.

E—Determination of the Consensus Sequence SEQ ID No. 3

Using computerized searching of sequence data bases (Genbank and EMBL), it has been shown that the sequence of the delta-7Red protein of $A.$ $thaliana$ had some sequence similarities with other sterol reductases, particularly sterol C-14 reductase and sterol C-24(28) reductase of $S.$ $cerevisiae$ described by Lorentz et al. (DNA Cell Biol., Vol. 11, pp. 685–692, 1992) and Chen et al. (Yeast, Vol. 7, pp. 305–308, 1991) respectively as well as the product of the sts 1+ gene of $S.$ $pombe$ described by Shimanuki et al. (Mol. Biol. Cell, Vol. 3, pp. 263–273, 1992) and sterol C-14 reductase of Neurospora crassa (No. X77955 in the EMBL database). In addition, the delta-7Red protein showed a similarity with the 400 amino acids of the C-terminal end of the chicken lamine B receptor and with that of the corresponding human receptor described by Worman et al. (J. Cell Biol., Vol. 111, pp. 1535–1542, 1990) and Schuler et al. (J. Biol. Chem., Vol. 269, pp. 11312–11317, 1994).

Sequence identity alignments were established between the amino acid sequence SEQ ID No. 2 deduced from the delta-7Red cDNA obtained above and those of the three yeast sterol reductases and the two lamine B receptors, then a new consensus sequence having the amino acid sequence (SEQ ID No. 3):

```
Leu Leu Xaa Xaa Gly Trp Xaa Gly Xaa Xaa Arg Xaa Xaa Xaa Tyr
 1           5              10              15
``` in which Xaa in position 7 is Trp or Tyr and Xaa in position 12 is His or Lys, was defined to prepare oligonucleotides which can be used as primers to amplify, by PCR, new genomic DNA or cDNA sequences coding for a protein having a delta-5,7 sterol, delta-7 reductase activity.

F—Expression of the delta-7Red protein in Yeast.

a) construction of the expression vector delta-7/V8 inducible in yeast

The deletion of the non-coding regions of cDNA of pF22 was carried out by the PCR amplification using the following specific oligonucleotides:

5'CGCGGATCCA TGGCGGAGAC TGTACATTC 3' (SEQ ID No. 4) and

5'CAGGGTACCT CAATAAATTC CCGGAATG 3' (SEQ ID No. 5)

which were defined to introduce a BamH I restriction site immediately upstream of the initiation codon and a Kpn I site immediately downstream of the stop codon.

The cDNA was amplified starting from 1 ng of "delta7red/pUC9N cDNA" plasmid in the presence of 2 units of Pfu DNA polymerase and 0.2 μM of each of the above primers by using the following amplification conditions: 94° C., 10s; 52° C., 50s; 74° C., 90s; 33 cycles with the Stratagene PCR kit.

A fragment of approximately 1300 bp was obtained, then digested by the restriction enzymes BamH I and Kpn I and inserted into the BamH I and Kpn I sites of the $E.$ $coli/S.$ $cerevisiae$ pYeDP1/8-2 shuttle vector (called V8) described by Cullin et al. (Gene, Vol. 65, pp. 203–217, 1988). V8 carried the selection indicator URA3 and contained an expression cassette in the yeast containing the promoter GAL10/CYC1 and the terminator sequence of the PGK gene. The vector thus obtained, called delta-7/V8, allowed the inducible expression by galactose of the delta-7Red protein.

b) Production of the delta-7Red protein

The yeast strain FY 1679 (Mata) was transformed with the delta-7/V8 plasmid obtained above by using the lithium acetate method described by Gietz et al. (already quoted). The transformed yeast was cultured at 27° C., in the SGI selective medium described above, but in which the glucose concentration was 5 g/l, until a cell density saturation ($OD_{600}nm=12$) was obtained. The culture was then diluted by the addition of a volume of complete medium YP (10 g/l in yeast extract (Difco) and 10 g/l in bactopeptone (Difco)), then the addition of ethanol (1.5% v/v) as a source of carbon. When the growth had been allowed to reach a cellular concentration of at least $7 \times 10^7$ cells/ml, the expression of delta-7Red was induced by the addition of galactose at a concentration of 20 g/l. The induction was also carried out in an SLI selective minimum medium, which corresponded to the SGI medium in which the glucose was replaced by galactose (20 g/l) until a cellular concentration of $2 \times 10^7$ cells/ml was obtained.

c) Enzymatic test in vitro of the delta-5,7 sterol, delta-7 reductase activity

Expression of the delta-7Red protein was revealed by using an enzymatic test described by Taton et al. (Biochem. Bioph. Res. Commun., Vol. 181, pp. 465–473, 1991) but without an NADPH regeneration system, with microsomal or cytosolic cell preparations of the above induced yeast. The cellular fractions were obtained by mechanical rupture of the induced cells and isolation of the fractions by ultracentrifugation according to the method described by Urban et al. (Eur. J. Biochem., Vol. 222, pp. 843–850, 1994). The cells were collected, then washed twice with TE-KCl buffer (50 mM Tris-HCl, pH 7.4; 1mM EDTA, 0.1 M KCl) and resuspended in 0.6 M TE-sorbitol lysis buffer. Glass beads with a diameter of 0.45–0.5 mm (Braun) were added until they showed through the surface of the cellular suspension which was then stirred for 5 minutes at 4° C. The cellular lysate on the surface was collected and the glass beads were washed three times with the lysis buffer. The lysate and the washings were combined and then centrifuged at 20,000 g for 13 minutes at 4° C. to eliminate the mitochondrial fractions. The collected supernatant was centrifuged for 1 hour at 100,000 g and at 4° C. The pellet which contained the microsomal fraction and the supernatant which represented the cytosolic fraction were collected separately.

The microsomal fraction or the cytosolic fraction obtained were incubated respectively for 90 minutes at 37° C. in 100 mM Tris/HCl buffer at pH 7.3 containing as substrate 150 μm of 7-dehydro-cholesterol emulsified with Tween 80 (1.5 g/l) and in the presence of 2 mM of NADPH. The sterols were extracted by the addition of 3 volumes of a methanol-dichloromethane mixture (50:50, v/v), then analyzed by GC in comparison with standard products. The formation of cholesterol (RT=15.887 min) from 7-dehydro-cholesterol (RT=16.528 min) is shown in FIG. 4 with a microsomal fraction (3.5 mg/ml of protein) obtained above from the yeast FY 1679 transformed with the delta-7/V8 vector, induced for 3 hours and the endogenous sterols of which have higher retention times (RT=16.682 min for ergosta 5-22 diene 3-ol; RT=17.249 min for ergosterol and RT=17.664 min for ergosta 5-ene 3-ol).

These results show that the delta-7Red protein, on the one hand was expressed in the transformed yeast, and on the other hand had a delta-5,7 sterol, delta-7 reductase activity.

EXAMPLE 2

Reduction in vivo of Endogenic Sterols of Yeast Unsaturated in Position C-7

Yeast strains whose majority sterols had a double bond in position C-5,7 were transformed with the delta-7/V8 vector obtained in Example 1, then cultured and induced as indicated in Example 1. The endogenic sterols, whose profile was analyzed by GC, were extracted and purified by RP-HPLC as indicated in Example 1 by using a preparative C18 column (100×4.6 mm), then identified by IR, UV, MS and NMR. The following three strains were used respectively:

Strain FY1679 described in Example 1;

Mutant strain erg5, called PLC 1051, characterized by a deficiency in sterol C-22 desaturase, which was constructed by crossing between the strain FY1679 and the original strain pol5 described by Molzahn et al. (J. Gen. Microbiol., Vol. 72, pp. 339–348, 1972) and which accumulated the ergosta 5,7-diene 3-ol.

The mutant double strain erg4,5, called PLC 1451, characterized by a deficiency in sterol C-22 desaturase (erg5) and sterol C-24(28) reductase (erg4), was obtained by crossing between the strain FY1679 and a strain pol5 described by Molzahn et al. (already quoted) having acquired a spontaneous resistance to nystatin during a systematic screening of yeasts searching for mutants of sterols and which accumulated ergosta 5,7,24(28) triene 3-ol. The resultant haploid strain, which carried the double mutation erg4, erg5, grew in the presence of galactose and a non-fermentable substrate and was auxotrophic for uracil, tryptophan and histidine. The strains PLC 1051 and PLC 1451 were deposited at the CNCM on Feb. 10th 1995 under the numbers I-1536 and I-1537, respectively.

The major reduced sterols identified respectively from the above three transformed strains are indicated in the following table:

| Initial strain. | Initial major endogenic sterol | Major endogenic sterol reduced in position C-7 |
| --- | --- | --- |
| FY 1679 | ergosta 5,7,22 triene 3-ol (ergosterol) | ergosta 5-ene 3-ol (dihydrobrassicasterol) ergdsta 5,22 diene 3-ol (brassicasterol) |
| erg5 PLC 1051 | ergosta 5,7 diene 3-ol | ergosta 5-ene-3-ol |
| erg4,5 PLC 1451 | ergosta 5,7,24 (28) triene-3-ol | ergosta 5,24 (28) diene 3-ol (ostreasterol) |

EXAMPLE 3

Production of Pregnenolone in vitro by Cleavage of Yeast Endogenic Sterols Reduced in Position C-7

Production of pregnenolone was carried out by using the enzymatic cleavage test of the side chain of cholesterol in vitro described by Wada et al. (Arch. Biochem. Biophys., Vol. 290, pp. 376–380, 1991) in which 260 μM of a sterol reduced in position C-7 obtained in Example 2 were incubated in 150 μl of 10 mM phosphate buffer, pH 7.4, 100 mM NaCl, 0.3% Tween 20 in the presence of 140 nM of adrenodoxin reductase, 1.16 μM of adrenodoxin and 0.68 μM of cytochrome $P_{450}SCC$ of bovine origin obtained from the suprarenal glands according to Seybert et al., J. Biol. Chem., Vol. 254, pp. 12088–12098, 1979.

The reaction was triggered by the addition of 150 μM of NADPH. After incubation for 80 min at 37° C., the reaction was stopped by the addition of a volume of a methanol-dichloromethane mixture (50:50 v/v) . The sterols were extracted and analyzed by GC as indicated in Example 1.

FIG. 5 shows respectively that ergosta 5-ene 3-ol (FIG. 5A), ergosta 5,24 (28) diene 3-ol (FIG. 5B) or ergosta 5,22 diene 3-ol (FIG. 5C) was the substrate of cytochrome $P_{450}SCC$ and led to a product having an identical RT to that of pregnenolone obtained under the same conditions by cleavage of cholesterol. The results obtained show that a transformed yeast expressing delta-7Red accumulates usable sterols directly to prepare pregnenolone by biological oxidation in vitro.

EXAMPLE 4

Construction of Yeast Strains Producing Pregnenolone or its Acetic Ester in vivo A—Construction of the Strain ELR01 containing an Expression Cassette for the delta-7Red of A. thaliana Integrated in the Locus ADE2 of the Haploid Strain FY1679 Mating Type a (FY1679 Nata)

a) Construction of the integrative plasmid pADdelta-7 (pADAΔ7):

Construction of the plasmid pAD Δ7 was carried out as described in FIG. 6. The BglII fragment (2244 pb) containing the ADE2 gene of S. cerevisiae was isolated from the plasmid pASZ 11 (Stotz et al., Gene, Vol. 95, p. 91, 1990) and inserted in the pBluescriptII KS+ vector (Stratagene) at the BamHI site of the multiple cloning site.

The plasmid obtained, called pBS-ADE2, was then linearized at its single Stu I site and dephosphorylated. A fragment of approximately 2.44 kb containing the promoter GAL10/CYC1, the coding phase of delta-7Red (sterol Δ7 reductase) and the terminator PGK (tPGK) was obtained from the plasmid delta-7/V8, obtained in Example 1F by the PCR technique using the following oligo-nucleotides as primers:

5'GATTACGCCA AGCTTTTCGA AAC 3' (SEQ ID No. 6) and
5'AGATCTTGAG AAGATGCGGC CAGCAAAAC 3' (SEQ ID N o. 7) which have been defined to pair with the 3' end of tPGK and the 3' end of the URA3 gene, respectively. The following were used: the plasmid delta-7/V8 as a template (80 ng), the above oligo-nucleotides (0.5 μM each), native Pfu DNA polymerase (1 unit in the buffer recommended by Stratagene) and the following amplification conditions: 35 cycles; 1 min at 95° C.; 5 sec. at 95° C.; 30 sec. at 56° C; 4 min 30 sec. at 70° C.). The amplification fragment obtained was then cloned at the blunt ends in the above linearized plasmid pBS-ADE2 to give the plasmid pADΔ7 in which the NotI-PstI fragment of approximately 4720 pb carries the ADE2 gene interrupted by the expression cassette of delta-7Red.

b) Chromosomic integration in the yeast strain FY1679 Hata:

The NotI-PstI fragment (4720 bp), isolated from the plasmid pADΔ7 digested with the restriction enzymes. NotI and PstI, was introduced into the yeast FY1679 Mata by transformation using the lithium acetate method described by Gietz et al. (already quoted). The transformants having integrated this fragment by homologous recombination were selected by their resistance to nystatin, this phenotype being due to the expression of delta-7Red which converted the delta-5,7 sterols of the yeast into delta-5 sterols.

The transformed cells were incubated at 28° C. for 4 hours in the complete medium YP described in Example 1F containing glucose (20 g/l) and supplemented with adenine (20 mg/l). They were then concentrated and plated on an SLI-agar minimum medium (1 g/l of bactocasaminoacids; 7 g/l of "yeast nitrogen base"; 20 g/l of galactose; 20 mg/l of adenine; 20 g/l of agar) and incubated overnight at 28° C. to induce the expression of the delta-7Red gene. The absence of uracil complementation allowed the growth of cells to be limited. The clones were collected, grouped and then plated on dishes on a complete medium YP containing galactose (20 g/l), supplemented with adenine (20 mg/l) and in the presence of increasing concentrations of nystatin (0 μg/ml, 1 μg/ml, 2 μg/ml, 5 μg/ml, 20 μg/ml respectively). On the 4th day, about twenty clones having grown at a concentration of 5 μg/ml of nystatin were obtained. Twelve of these clones were sub-cultured on dishes in minimum medium Wo (7g/l of "yeast nitrogen base" without amino acids, 20 g/l of glucose) enriched with uracil, leucine, tryptophan, histidine and adenine (20 mg/l each).

The auxotrophy of the adenine due to the disruption of the ADE2 gene was then confirmed by observing the absence of growth on the minimum medium Wo described above enriched with uracil, leucine, tryptophan, histidine but free of adenine. The presence of the expression cassette in the genome of the yeast was controlled by PCR amplification from the genomic DNA of the clones obtained and by using the primers having the sequence SEQ ID No. 6 and SEQ ID No. 7 above.

The functionality of the in tegrated delta-7Red gene was confirmed by GC analysis of the composition in sterols accumulated in the yeast and extracted by alkaline saponification according to the operating method of Example 1B with a five meter SE 30 capillary column (Alltech). Analysis showed a modified profile containing sterols saturated in position C-7 when the clones were cultivated in the presence of galactose. The strain obtained, called ELR01, accumulated ergosta 5 ene 3-ol and ergosta 5,22 diene 3-ol instead of ergosta 5, 7, 22 triene 3-ol (ergosterol), the majority sterol of the initial strain FY1679 as is shown in FIG. 7.

The strain ELR01 constructed in this way expressed the delta-7Red gene when it was cultured in the presence of galactose due to transcriptional control by the promoter GAL10/CYC1. Although the expression unit for delta-7Red had the same transcription direction as that of the ADE2 gene, no expression of the delta-7Red was detectable by analysis of the composition of sterols by GC when the culture was carried out in the presence of glucose, as a result of the repression of the promoter GAL10/CYC1.

B—Construction of the Strain CDR01 Containing an Expression Cassette for the Mature form of bovine adrenodoxin reductase (ADRm) Integrated Between the loci LEU2 and SPL1 of the Haploid Strain FY1679 Mating Type alpha (mat. alpha).

a) Construction of the shuttle vector E. coli-S. cerevisiae V13 The V13 vector corresponds to the V8 vector (Cullin et al., already quoted) which carries the selection indicator URA3 and an expression cassette in yeast containing the GAL01/CYC1 promoter (pG/C) and in which an additional SalI site (Sa) had been introduced into the multiple cloning site, according to the construction diagram given in FIG. 8. The V8 vector was digested by the restriction enzymes HindIII and BamHI and the BamHI-HindIII fragment obtained (1722 pb) containing the URA3 gene and the GAL10/CYC1 promoter (called further on ura-gal"), was sub-cloned between the corresponding sites of the pUC18 vector (Pharmacia) digested by the restriction enzymes HindIII and BamHI.

The "ura-gal" fragment was then amplified by PCR from 30 ng of the pUC18/"lura-gal" plasmid obtained denatured for 30 sec. at 95° C. using the following conditions: 30 cycles; 5 sec. at 86° C.; 10 sec. at 95° C.; 40 sec. at 38° C.; 5 sec. at 55° C. and 2 min at 74° C.), 2 units of Tag DNA polymerase (Boehringer) in the manufacturer's buffer and 1 μM of each of the primers having the following nucleotide sequences:

5' GGGGATCCGT GGTCGACGTA ATTTAGTGTG TGTATTTGTG TTTGCG 3' (SEQ ID No. 8) and

5' GTAAAACGAC GGCCAGT 3' (SEQ ID No. 9)

The primer SEQ ID No. 8 contained a BamHI GGATCC site identical to that of the "ura-gal" fragment, 3 consecutive nucleotides at the BamHI site not hybridizing with the template, an SalI GTCGAC site and a sequence homologous to that of the GAL10/CYC1 promoter. The primer SEQ ID No. 9 matched the sequence preceding the Hind III site of the multiple cloning site pUC18, The HindIII-BamHI fragment of 1722 pb obtained after amplification was digested by XhoI and Bam HI, releasing a fragment of 254 bp containing the GAL10/CYC1 promoter (pG/C) which was then sub-cloned in the V8 vector digested by the restriction enzymes BamHI and XhoI.

The resultant V13 vector contained restriction sites allowing easy sub-cloning of the cDNA's coding for mature bovine adrenodoxin reductase (ADRm), mature bovine adrenodoxin (ADXm) and the bovine cytochrome $P_{450}$SCC. Starting from the V13 vector, the V13-ADR vector, the V13-ADX vector and the V13-SCC10 vector were prepared respectively in the following manner:

a) Construction of the V13-ADR vector

A SalI-KpnI fragment of 1478 pb carrying the cDNA coding for ADRm was isolated from the plasmid pGBADR-2 described in Example 25 of European Patent Application EP 340878 and sub-cloned in the corresponding sites of the V13 vector to give the V13-ADR vector.

b) Construction of the V13-ADX vector

A SalI BamHI fragment of 390 pb carrying the cDNA coding for ADXm was isolated from the plasmid pGBADX-1 described in Example 23 of European Patent Application EP 340878 and sub-cloned in the corresponding sites of the V13 vector to give the V13-ADX vector.

c) Construction of the V13-SCC10 vector

A SalI-EcoRI fragment of 1554 pb carrying the cDNA coding for $P_{450}$SCC was isolated from the plasmid pGBSCC-10 described in Example 6 of European Patent Application EP 340878 and sub-cloned in the corresponding sites of the V13 vector to give the V13-SCC10 vector.

b) Construction of the Integrative Plasmids pCD62-1 and pCD62-2:

The construction of the plasmids pCD62-1 and pCD62-2 was carried out as described in FIG. 9.

a) Construction of the plasmid pFL26CD

A NotI site was introduced into the plasmid pFL26 (Bonneaud et al., Yeast, Vol. 7, pp. 609–615, 1991), in the intergenic region separating the leu2 gene from the 5' end of the spl1 gene (called spl1Δ) (Kolman et al., J. Bacteriol., Vol. 175, p. 1433, 1993) according to the following operating method:

Two DNA fragments of 704 bp and 347 bp carrying the 5' end of leu2 and the 3' end of Spl1Δrespectively were synthesized by PCR using primers having the following nucleotide sequences:

5' TTGAAGGTTC AACATCAATT GATTG 31' (SEQ ID No. 10) and

5' GTGTGGCGGC CGCCTCCTTG TCAATATTAA TGT-TAAAG 3' (SEQ ID No. 11)

for the amplification of the 704 bp fragment and the nucleotide, sequences

5' CAAGGAGGCG GCCGCCACAC AAAAAGTTAG GTGT 3' (SEQ ID No. 12) and

5' TCTGCTTCCC TAGAACCTTC TTATG 3' (SEQ ID No. 13)

for the amplification of the 347 bp fragment.

The primers SEQ ID No. 11 and SEQ ID No. 12 had a sequence GGCGGCCG which corresponded to a NotI site and in which 3 bases do not match with the template. The primer SEQ ID No. 10 matched with a sequence situated 536 bp upstream from the stop codon of leu2 and the primer SEQ ID No. 13 with a sequence situated 194 bp upstream that of spl1Δ.

The 704 bp and 347 bp fragments were first amplified by PCR by using the plasmid pFL26 as the template and Pfu DNA polymerase as the enzyme under standard conditions described by the supplier (Stratagene). The two amplified fragments obtained matched over 20 bp at the level of the ends generated by the primer SEQ ID No. 11 (704 bp fragment) and the primer SEQ ID No. 12 (347 bp fragment) starting from the 5' end; these 20 bp correspond to the first 20 nucleotides of each of these primers, respectively.

The product resulting from the pairing of the DNA fragments of 704 bp (1 ng) and 347 bp (2 ng) was amplified using primer SEQ ID No. 10 and SEQ ID No. 13 and the following conditions: 30 cycles of 10 sec. at 95° C., 5 sec. at 60° C., 1 min at 45° C., 5 sec. at 65° C. and 2 min at 72° C. followed by a cycle of 7 min at 72° C.; 50 pmol of each primer and 1 unit of Pfu DNA polymerase in 50 μl of reaction buffer (Stratagene). An amplified fragment of 1031 bp containing a NotI restriction site was obtained. This fragment was then digested by the BstXI and NsiI enzymes and the fragment of 920 bp obtained, containing the NotI site, was inserted in place of the initial BstXI-NsiI fragment of pFL26 to obtain the plasmid pFL26CD, whose map is represented in FIG. 9a.

b) Construction of the plasmid pCD60

Preparation of the plasmid pDP10036:

A SalI-BamHI fragment of 390 bp carrying the cDNA coding for mature bovine adrenodoxin (ADXm) was isolated from the plasmid V13-ADX, then sub-cloned in the SalI-BglII sites of the multiple cloning site of the plasmid pTG10033 which was flanked by the inducible promoter GAL10/CYC1 and the terminator ter PGK. The plasmid pTG10033, whose map was represented in FIG. 18 and which corresponded to the expression vector pTG10031 (FIG. 17), containing the promoter CYCL and terPGK, in which the promoter CYC1 had been replaced by the promoter GAL10/CYC1 was prepared according to the operating method described further on. The plasmid thus obtained, called pDP10034, carried the ADX expression cassette, i.e. the gene coding for ADXm under the transcriptional control of GAL10/CYC1 and terPGK. Subsequently, the term "expression cassette" will be used for any gene under the transcriptional dependence of GAL10/CYC1 and terPGK.

A HindIII fragment of 3593 bp carrying the selection indicator URA3 and the ADR expression cassette was isolated from the plasmid V13-ADR digested by the restriction enzyme HindIII, then inserted in the corresponding site of plasmid pDP10034 digested by the restriction enzyme HindIII. The plasmid obtained, called pDP10036, contained the ADX and ADR expression cassettes separated from each other by the marker URA3 (FIG. 9b).

Preparation of the plasmid pCD60:

The AflIII-AccI fragment of 2770 bp carrying the ADR cassette was isolated by partial digestion of the plasmid pDP10036 with the restriction enzymes AflIII and AccI, and blunt ends were created by treatment with the klenow fragment of DNA polymerase I and sub-cloned after ligation at the blunt ends in the SmaI site of the plasmid pBlue-Script KS+ (Stratagene). In the plasmid obtained, called pCD60, the ADR expression cassette was framed on either side by a NotI site, one situated at 209 bp upstream of the AflIII/SmaI ligation site and originating from the sub-cloned fragment and the other originating from the multiple cloning site (MCS1) of pBlue-Script KS+ (FIG. 9b).

c) Construction of plasmids pCD62-1 and pCD62-2:

The NotI fragment of 2558 bp, isolated from the plasmid pCD60 digested by the restriction enzyme NotI, was then sub-cloned in the single NotI site of the plasmid pFL26CD. Depending on the direction of the insertion of the fragment, two plasmids were obtained, called pCD62-1 and pCD62-2 (FIG. 9c). In the plasmid pCD62-1, the ADR expression cassette was oriented in the direction of the transcription of the leu2 gene while this orientation was reversed in the plasmid pCD62-2. The plasmid pCD62-1 was retained for subsequent constructions.

c) Chromosomic Integration in the Yeast Strain FY1679 (Matalpha):

The plasmid pCD62-1 contained regions homologous to a chromosomic locus of the strain FY1679. These regions corresponded respectively to fragments BglII-ClaI of 1060 bp (A), EcoRI-NotI of 707 bp (B) and NotI-BglII of 602 bp (C) indicated in FIG. 10. The region corresponding to the ClaI-EcoRI fragment of 486 bp of the plasmid pCD62-1 was deleted in the strain FY1679, implying an auxotrophy of this strain vis-a-vis leucine (strain LEU2) (R. S. Sikorski et al., Genetics, 122, 19, 1989). The plasmid pCD62-1 was linearized by digestion with the restriction enzyme XbaI whose restriction site was situated outside the homologous regions and then was introduced by transformation in the strain FY1679 (Matalpha) using the lithium acetate method (D. Gietz et al., already quoted).

The cellular repair capacity of the DNA by the yeast ("gap repair") and the selection of recombinants having the phenotype LEU2$^+$ allowed in the first instance two types of recombinants to be selected: the 1st type was obtained after homologous recombinations at the level of fragments A and B and the 2nd type was obtained after homologous recombinations at the level of fragments A and C. Only the latter type of recombination allowed the integration of the ADR expression cassette in addition to the restoration of phenotype LEU2$^+$. To select this 2nd type of clone, a screening by PCR was carried out using the primer SEQ ID No. 10 above and the primer having the following nucleotide sequence:
5' TACATTAGGT CCTTTGTAGC 3' (SEQ ID No. 14)
so as to confirm both the presence and the correct localization of the ADR expression cassette in the genome of the strain FY1679 (Matalpha).

In this screening, the primer SEQ ID No. 14 exclusively matched the sequence coding for ADRm and the primer SEQ ID No. 10 matched a chromosomic sequence (FIG. 10). The amplification reaction was carried out using as template the genomic DNA (20 ng) isolated from the strain FY1679 (Matalpha) (Hoffman et al., Gene, Vol. 57, p. 267, 1987), Taq DNA polymerase (1U, Boehringer), 50 pmol of each primer and 30 PCR cycles (10 sec. at 95° C., 1 min at 55° C., 3 min at 72° C.) under the standard conditions described by the supplier. The amplification led to the isolation of a corresponding fragment of 2.9 kb in the case where the expression cassette had been integrated. In the opposite case, no amplification product was detected. The strain FY1679 (Matalpha) selected in this way containing the ADR integrated expression cassette was called CDR01.

The expression of ADR by this strain was revealed from cytosolic cellular fractions prepared according to the protocol described in Example 1F, by immunodetection of the protein recognized by the anti-ADR antibodies. The functionality of the ADR expressed by the strain CDR01 was confirmed in the enzymatic cleavage test of the side chain of cholesterol in vitro described in Example 3 and in which the purified ADR (0.28 pmol) was replaced by a cytosolic cellular fraction of the strain CDR01 containing 100 ug of total proteins. A bioconversion rate of cholesterol into pregnenolone of approximately 25% was observed, comparable to that obtained with purified ADR.

C—Construction of the Diploid Strain EC01 Coexpressing Delta-7Red of *A. Thaliana* and ADRM.

The diploid strain EC01 was obtained by crossing the haploid strains CDR01 and ELR01 obtained above according to the protocol described by Sprague et al. (Methods in Enzymology, Vol. 194, p. 77, 1991): A first selection on minimum medium WO described previously, enriched with uracil, tryptophan and histidine (20 mg/l each) but free of leucine, allowed the diploid clones LEU2$^+$ (prototrophic character which showed the presence of the ADR expression cassette) to be isolated. These clones were then tested for their resistance to nystatin at 5 μg/ml (resistance character which shows the presence of the expression cassette for delta-7Red) on the solid synthetic SLI-agar medium described previously. A strain, called EC01, was in this way arbitrarily isolated from the clones resistant to nystatin.

D—Construction of the Strain EC01/pCD63 Producing Pregnenolone and Pregnenolone 3-acetate.

a) Construction of the expression plasmid pCD63

The construction of the plasmid pCD63 was carried out as described in FIG. 11. The NotI fragment of 4961 bp containing the ADX expression cassette, the selection indicator URA3 and the ADR expression cassette, were isolated from the plasmid pDP10036 prepared above and digested with the restriction enzyme NotI and then cloned in the NotI site of the multiple cloning site of plasmid pFL45L (Bonneaud et al., Yeast, Vol. 7, p. 609, 1991). The vector thus obtained, called pDP10037, is represented in FIG. 11.

On the one hand, the plasmid pDP10037 was linearized by digestion with the enzyme Tth111I whose restriction site was situated in the gene coding for ADRm. On the other hand, a PvuII-EcoRV fragment of 3476 bp containing the expression cassette for P$_{450}$SCC and the 5' end of the URA3 marker were purified from the plasmid V13-SCC10 obtained previously and digested with the restriction enzymes PvuII and EcoRV. The two linear DNA's respectively obtained had homologous regions which correspond on the one hand to the 5' end of the gene URA3 and to GAL10/CYC1, on the other hand to ter PGK as represented in FIG. 11a.

These two fragments were then introduced into the yeast strain FY1679 (Mata) by co-transformation using the lithium acetate method (Gietz et al., already quoted). The following selection of prototrophic recombinants for uracil and tryptophan (URA3$^+$, RTP1$^+$), allowed clones to be isolated in which the double strand break generated by digestion by the restriction enzyme Tth111I had been repaired as a result of the integration of the expression cassette P$_{450}$SCC by homologous recombination.

Selection of the recombinants (URA3$^+$, RTP1$^+$) was carried out on minimum medium WO enriched with leucine, histidine and leucine (20 mg/l each) but free from uracil and tryptophan. Starting from 50 collected clones, the total DNA was extracted by the method described by Hoffman et al., (Gene, Vol. 57, p. 267, 1987), then introduced by electroporation into the strain of *E. coli* XL1-Blue (Stratagene). The clones transformed by the plasmid generated by "gap repair" were selected on the rich medium LB (tryptone 1%, yeast extract 0.5%, NaCl 1%) containing 50 mg/l of ampicillin. Starting from one of the selected clones, the plasmid, called pCD63, was extracted according to the method described by Sambrook et al., Molecular Cloning, Cold Spring Harbor Laboratory Press, 1989. The plasmid pCD63 obtained contained expression cassettes ADX and $P_{450}SCC$ separated by the selection indicator URA3, as represented in FIG. 11b.

b) Transformation of the strain EC01 by the plasmid pCD63

The plasmid pCD63 was introduced into the strain EC01 obtained above by transformation by the lithium acetate method (Gietz et al., already described). The transformed yeast was then cultured on the minimum medium WO described previously and free from uracil, tryptophan, adenine and leucine but supplemented with histidine (20 mg/l). The strain, called EC01/pCD63, was isolated in this way. A sample of the strain, under the reference EC01/pCD63, was deposited at the CNCM on 10th February 1995 under the number I-1538.

c) Production in vivo of pregnenolone and pregnenolone 3-acetate.

The strain EC01/pCD63 was cultured at 28° C. under aerobic conditions (130 r/min) in a 3-liter Erlenmeyer flask until the stationary growth phase was reached (OD600 nm=12 to 13) in the selective medium SGI described in Example 1A and in which the glucose concentration was 5 g/l. The culture was then diluted by the addition of a volume of the complete medium YP described above and then the addition of ethanol (0.5% v/v) as a source of carbon. When a new stationary growth phase had been reached (OD600 nm=12 to 13), galactose (20 g/l) was added to the culture in the form of a concentrated solution (500 g/1), so as to simultaneously induce the expression of genes coding for ADXm, ADRm, $P_{450}SCC$ and delta-7 Red which were respectively under the control of the promoter GAL10/CYC1.

The co-expression of the four genes was revealed by analysis of the sterols accumulated in the cells and in the supernatant of the culture respectively according to the following operating method: 50 ml samples of the culture were harvested after 9 hours and 24 hours of induction and each sample was centrifuged (4000 g, 10 min, 4° C.) to separate the cells from the culture medium. On the one hand, 24 hours of induction are shown in FIG. 12a and in FIG. 12b, respectively.

After 9 hours of induction, FIG. 12a shows: in the cellular lysate, the presence of a majority compound having an identical retention time to that of standard pregnenolone acetate (RT=11.8 min) while only a very weak peak was present at the retention time of the pregnenolone (RT=9.9 min). Low quantities of endogenic sterols of the yeast reduced in position C-7 (ergosta 5-ene 3-ol and ergosta 5,22 diene 3-ol) were identified respectively at RT=18 min and RT=17 min. The alkaline saponification of the cellular lysate before analysis led to the presence of a majority compound co-migrating with the pregnenolone. This allowed confirmation that the accumulated compound having an RT of 11.8 min corresponds to pregnenolone acetate in the culture medium, the significant absence of pregnenolone or its acetate was shown.

After 24 hours of induction, FIG. 12b shows: in the cellular lysate, the presence of low quantities of pregnenolone (RT=10.2 min) and of pregnenolone acetate (RT=12 min) as well as of reduced endogenic sterols of the yeast (RT=17 min and RT=18 min). The cholesterol (RT=16.2 min) was an internal standard added before the extraction. In the culture medium, the majority presence of pregnenolone acetate and a minor quantity of pregnenolone was shown.

The experiments carried out in parallel with the strain EC01 transformed by a control plasmid such as pFL45L already quoted, showed no peak corresponding to free pregnenolone or pregnenolone in the acetate form. Identification of the sterols carried out in this way showed that the yeast strain EC01/pCD63 had accumulated the pregnenolone and the pregnenolone acetate in the absence of any source of exogenic sterols, after induction in the presence of galactose with a major production after an induction of 9 hours. These results demonstrate on the one hand the effective mobilization of the endogenic sterols reduced in position C-7 of the strain EC01 and on the other hand, the extreme effectiveness of the coupling of the restriction reaction of the side chain of the endogenic sterols.

| Strains | Integration locus | Integrated gene | Transformant plasmid | Plasmid marker | Gene(s) on the plasmid | Selection indicators |
|---|---|---|---|---|---|---|
| CDR01 (Mata) | Intergenic LENO2-SPL1 | ADRm | — | — | — | HIS3, URA3, TRP1 |
| HLR01 (Mata) | ADDE2 | delta-7Red | — | — | — | ADE2, URA3, LEU2, HIS3, TRP1 |
| EC01 (diploid) | Intergenic LENO2-SPL1 + ADDE2 | ADRm delta-7Red | — | — | — | HIS3, URA3, TRP1 |
| EC01/ pCD63 | Intergenic LENO2-SPL1 + ADDE2 | ADRm delta-RED | pCD63 | URA3 TRP1 | ADXm P4SOCC | HIS3 | the cells were lyzed by mechanical rupture in the one hand, the cells were lyzed by mechanical rupture in the presence of glass beads according to the method indicated in Example 1F. Starting from the lysate thus obtained, the intracellular sterols were then extracted by the addition of a volume of hexane.

On the other hand, the sterols present in the culture medium were extracted directly by the addition of a volume of hexane. The composition of sterols extracted were analyzed by GC as indicated in Example 1, compared with standard products. The results obtained after 9 hours or after

PREPARATION OF EXAMPLE 4

Construction of the Plasmid pTG10033

1. Derivative of pUC19 having a New Multiple Cloning Site:

The cloning vector M13mp19 (C. Yanish-Peron et al., Gene, 33, 103, 1985) was mutagenized using the following oligonucleotide:

5' GCGCTCAGCG GCCGCTTTCC AGTCG 3' SEQ ID No. 15 to introduce a NotI site into the sequence of the truncated laci gene and to give the plasmid M13TG724. A "polylinker" containing the EcoRI, SnaBI and NotI sites was then introduced into the EcoRI site of the plasmid M13TG724 by using the following oligonucleotides:
5'AATTGCGGCC GCGTACGTAT G 3' SEQ ID No, 16 and
5'AATTCATACG TACGCGGCCG C 3' SEQ ID No. 17
to give the plasmid M13TG7244 in which a modification of the insert was observed during the amplification stage. The insert of the plasmid M13TG7244 has the following nucleotide sequence:
GAATTCATACGTACGCGGCCGCAATTGCGGCCGG
TACGTATAATTCACTGGCCGT
in which the EcoRI, SnaBI and NotI sites are underlined and the lacZ sequence of pUC19 is in italics.

After digestion of the plasmid M13TG7244 by the restriction enzymtes EcoRl and SstI, a "polylinker" containing the MluI and AvrII sites was introduced using the following oligonucleotides:
5'CAACGCGTCC TAGG 3' SEQ ID No. 18 and
5'AATTCCTAGG ACGCGTTGAG CT 3' SEQ ID No. 19.

After digestion with the enzyme PvuII, the PvuII fragment obtained was sub-cloned in pUC19 (Yanish-Porch et al. already quoted) to obtain the plasmid pTG7457 (FIG. 13).

2. Sub-cloning of the PGK Terminator:

pUC19 was digested with the restriction enzymes BamHI and EcoRI and a new "polylinker" BamHI SstI was introduced using the following oligonucleotides:
5'GATCCGCAGA TATCATCTAG ATCCCGGGTA GAT 3' SEQ ID No. 20,
5'AGAGCTCAAG ATCTACCCGG GATCTAGATG ATATCTGCG 3' SEQ ID No. 21,
5'CTTGAGCTCT ACGCAGCTGG TCGACACCTA GGAG 3' SEQ ID No. 22 and
5'AATTCTCCTA GGTGTCGACC AGCTGCGT 3' SEQ ID No. 23.

The plasmid pTG7453 was obtained in this way (FIG. 14) and then was digested by the restriction enzymes BamHI and SstI. The sites of the "polylinker" between BamHI and SstI were introduced into a derivative of plasmid pTG7457 obtained above and digested by the restriction enzymes BamHI and SstI. The new plasmid contains the PvuII, HindIII, BamHI, EcoRI, XbaI, SmaI, BglII, SstI (=SacI), MluI, AvrII, EcoRI, SnaBI, NotI, SnaBI, PvuI sites. This new plasmid was digested by the restriction enzymes BglII and HindIII and a BglII-HindIII fragment containing the PGK promoter (Hitzeman et al., Nucleic Acids Res., Vol. 10, p. 7791, 1982; Loison et al., Yeast, Vol. 5, p. 497, 1989) was inserted in the former to give the plasmid pTG10014 (FIG. 15).

3. Sub-cloning of Promoters:

a) the CYC1 promoter

The sites of the "polylinker" between BamHI and SstI of the plasmid pTG7453 were introduced into a derivative of the plasmid pTG7457 as indicated above. The new plasmid was restricted by the restriction enzyme SnaBI and then the RsaI-DraI fragment of 456 bp of the plasmid pEMBL8 (Dente et al., Nucleic Acid Res., Vol. 11, p. 1645, 1983) containing the origin of replication of the phage f1 was introduced to give the plasmid pTG7503. The BamHI HindIII fragment of 0.78 kb of plasmid pGBSCC-9, prepared in Example 6 of European Patent Application EP 0340378 and containing the CYC1 promoter of *S. cerevisiae*, a "polylinker" and the lactase terminator of *K.lactis*, was sub-cloned in the plasmid pTG7503 digested with the restriction enzymes HindIII and BamHI to obtain the plasmid pTG10004 (FIG. 16).

The XhoI and MluI sites of the CYC1 promoter were then. eliminated by site directed mutagenesis of the double strand DNA of the plasmid pTG10004 using the following oligonucleotide:

5'GCGGATCTGC TCGAAGATTG CCTGCGCGTT GGGCTTGATC 3' SEQ ID No. 24.

The plasmid pTG10005 obtained was then digested by the restriction enzymes SalI and XhoI and then a MluI site was introduced by using the following oligonucleotides:

5'TCGACGGACG CGTGG 3' SEQ ID No. 25 and
5'TCGACCACGC GTCC 3' SEQ ID No. 26 to give the plasmid pTG10006.

b) the GAL10/CYC1 promoter

The plasmid pYeDP1/8-2 (Cullin et al., Gene, Vol. 203, 1988) was opened with the restriction enzyme XhoI. The cohesive ends created were filled using the Klenow fragment of DNA polymerase and then the plasmid was religated. The plasmid pTG10010 obtained in which the GAL10/CYC1 promoter no longer contained the XhoI site was used as a template for a PCR amplification.

4. Construction of the Expression Vector pTG10031

The remaining part of the sequence coding for lacZ was eliminated in the plasmid pTG7503 by site directed mutagenesis using the following oligonucleotide:

5'TGGCCGTCGT TTTACTCCTG CGCCTGATGC GGTAT 3' SEQ ID No. 27 to obtain the plasmid pTG7549.

The LacZ promoter present in the plasmid pTG7549 was then deleted using the following oligonucleotides:

5'GGCCGCAAAA CCAAA 3' SEQ ID No. 28 and
5'AGCTTTTGGT TTTGC 3' SEQ ID No. 29 which were inserted in the plasmid digested first with the restriction enzymes NotI and HindIII and which restored the two sites to give the plasmid pTG7553.

A BamHI MluI fragment containing the CYC1 promoter was obtained from the plasmid pTG10006 digested by the restriction enzymes BamHI and MluI and a MluI HindIII fragment containing the PGK promoter was isolated from the plasmid pTGC10015 digested by the restriction enzymes MluI and HindIII. These two fragments were ligated and the ligation product obtained was inserted in the plastid pTG7553 digested beforehand by the restriction enzymes MluI and HindIII.

The following oligonucleotide:

5'CTATCGA TGCGGCCGCG 3' SEQ ID No. 30 hybridized with the following oligonucleotide:

5'GCGCGGC CGCATCGATA 3' SEQ ID No. 31 which constituted a BamHI MluI "linker" containing the ClaI and NotI sites, was added and ligated to give the expression vector pTG 10031 (FIG. 17). The fragment amplified by PCR obtained from the and pYeDP1/8-2 was digested with the restriction enzymes ClaI and SalI and then was introduced into the plasmid pTG10031 digested beforehand with the same restriction enzymes to give the plasmid pTG10033 (FIG. 18).

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
       (A) LENGTH: 1496 base pairs
       (B) TYPE: nucleic acid
       (C) STRANDEDNESS: single
       (D) TOPOLOGY: linear (ii) MOLECULE TYPE: cDNA (vi) ORIGINAL SOURCE:
       (A) ORGANISM: Arabidopsis thaliana (ix) FEATURE:
       (A) NAME/KEY: CDS
       (B) LOCATION:76..1365

(xi) SEQUENCE DESCRIPTION: SEQ ID NO: 1:

```
GTGTGAGTAA TTTAGGTCAA CACAGATCAG AATCTGAGGC TTTGGCCGAG ACGAAGAGAA        60

AAGCAGAAGA AGAAA ATG GCG GAG ACT GTA CAT TCT CCG ATC GTT ACT TAC       111
                 Met Ala Glu Thr Val His Ser Pro Ile Val Thr Tyr
                  1               5                  10

GCA TCG ATG TTA TCG CTT CTC GCC TTC TGT CCA CCT TTC GTC ATT CTC        159
Ala Ser Met Leu Ser Leu Leu Ala Phe Cys Pro Pro Phe Val Ile Leu
         15                  20                  25

CTA TGG TAC ACA ATG GTT CAT CAG GAT GGT TCT GTT ACT CAG ACC TTT        207
Leu Trp Tyr Thr Met Val His Gln Asp Gly Ser Val Thr Gln Thr Phe
     30                  35                  40

GGC TTC TTT TGG GAG AAT GGA GTT CAA GGA CTT ATC AAC ATA TGG CCA        255
Gly Phe Phe Trp Glu Asn Gly Val Gln Gly Leu Ile Asn Ile Trp Pro
 45                  50                  55                  60

AGA CCC ACT TTG ATT GCT TGG AAA ATT ATA TTT TGC TAT GGA GCA TTT        303
Arg Pro Thr Leu Ile Ala Trp Lys Ile Ile Phe Cys Tyr Gly Ala Phe
                 65                  70                  75

GAA GCT ATT CTT CAG CTG CTT CTG CCT GGT AAA AGA GTT GAG GGT CCA        351
Glu Ala Ile Leu Gln Leu Leu Leu Pro Gly Lys Arg Val Glu Gly Pro
             80                  85                  90

ATA TCT CCA GCC GGA AAC CGA CCA GTT TAC AAG GCC AAT GGT CTG GCT        399
Ile Ser Pro Ala Gly Asn Arg Pro Val Tyr Lys Ala Asn Gly Leu Ala
         95                  100                 105

GCT TAC TTT GTG ACA CTA GCA ACC CAT CTT GGT CTT TGG TGG TTT GGA        447
Ala Tyr Phe Val Thr Leu Ala Thr His Leu Gly Leu Trp Trp Phe Gly
     110                 115                 120

ATC TTC AAC CCT GCA ATT GTC TAT GAT CAC TTG GGT GAA ATA TTT TCG        495
Ile Phe Asn Pro Ala Ile Val Tyr Asp His Leu Gly Glu Ile Phe Ser
125                 130                 135                 140

GCA CTA ATA TTC GGA AGC TTC ATA TTT TGT GTT TTG TTG TAC ATA AAA        543
Ala Leu Ile Phe Gly Ser Phe Ile Phe Cys Val Leu Leu Tyr Ile Lys
                 145                 150                 155

GGC CAT GTT GCA CCT TCA TCA AGT GAC TCT GGT TCA TGT GGT AAC CTA        591
Gly His Val Ala Pro Ser Ser Ser Asp Ser Gly Ser Cys Gly Asn Leu
             160                 165                 170

ATA ATT GAC TTC TAT TGG GGC ATG GAG TTG TAC CCT CGA ATT GGT AAG        639
Ile Ile Asp Phe Tyr Trp Gly Met Glu Leu Tyr Pro Arg Ile Gly Lys
         175                 180                 185

AGC TTT GAC ATC AAG GTG TTT ACT AAT TGC AGA TTC GGA ATG ATG TCT        687
Ser Phe Asp Ile Lys Val Phe Thr Asn Cys Arg Phe Gly Met Met Ser
     190                 195                 200
```

```
TGG GCA GTT CTT GCA GTC ACG TAC TGC ATA AAA CAG TAT GAA ATA AAT    735
Trp Ala Val Leu Ala Val Thr Tyr Cys Ile Lys Gln Tyr Glu Ile Asn
205                 210                 215                 220

GGC AAA GTA TCT GAT TCA ATG CTG GTG AAC ACC ATC CTG ATG CTG GTG    783
Gly Lys Val Ser Asp Ser Met Leu Val Asn Thr Ile Leu Met Leu Val
                225                 230                 235

TAT GTC ACA AAA TTC TTC TGG TGG GAA GCT GGT TAT TGG AAC ACC ATG    831
Tyr Val Thr Lys Phe Phe Trp Trp Glu Ala Gly Tyr Trp Asn Thr Met
            240                 245                 250

GAC ATT GCA CAT GAC CGA GCT GGA TTC TAT ATA TGC TGG GGT TGT CTA    879
Asp Ile Ala His Asp Arg Ala Gly Phe Tyr Ile Cys Trp Gly Cys Leu
        255                 260                 265

GTG TGG GTG CCT TCT GTC TAC ACT TCT CCA GGC ATG TAC CTT GTG AAC    927
Val Trp Val Pro Ser Val Tyr Thr Ser Pro Gly Met Tyr Leu Val Asn
    270                 275                 280

CAC CCC GTC GAA CTC GGA ACT CAG TTG GCA ATA TAC ATT CTC GTT GCA    975
His Pro Val Glu Leu Gly Thr Gln Leu Ala Ile Tyr Ile Leu Val Ala
285                 290                 295                 300

GGA ATT CTG TGC ATT TAC ATA AAG TAT GAC TGT GAT AGA CAA AGG CAA    1023
Gly Ile Leu Cys Ile Tyr Ile Lys Tyr Asp Cys Asp Arg Gln Arg Gln
                305                 310                 315

GAG TTC AGG AGG ACA AAC GGG AAA TGT TTG GTT TGG GGA AGA GCC CCG    1071
Glu Phe Arg Arg Thr Asn Gly Lys Cys Leu Val Trp Gly Arg Ala Pro
            320                 325                 330

TCA AAG ATT GTG GCG TCG TAT ACT ACA ACA TCT GGT GAA ACT AAA ACT    1119
Ser Lys Ile Val Ala Ser Tyr Thr Thr Thr Ser Gly Glu Thr Lys Thr
        335                 340                 345

AGT CTT CTC TTA ACG TCT GGA TGG TGG GGA TTG GCT CGT CAT TTC CAT    1167
Ser Leu Leu Leu Thr Ser Gly Trp Trp Gly Leu Ala Arg His Phe His
    350                 355                 360

TAT GTT CCT GAG ATC TTA AGT GCT TTC TTC TGG ACC GTA CCG GCT CTC    1215
Tyr Val Pro Glu Ile Leu Ser Ala Phe Phe Trp Thr Val Pro Ala Leu
365                 370                 375                 380

TTC GAT AAC TTC TTG GCA TAC TTC TAC GTC CTC ACC CTT CTT CTC TTT    1263
Phe Asp Asn Phe Leu Ala Tyr Phe Tyr Val Leu Thr Leu Leu Leu Phe
                385                 390                 395

GAT CGA GCC AAG AGA GAC GAT GAC CGA TGC CGA TCA AAG TAT GGG AAA    1311
Asp Arg Ala Lys Arg Asp Asp Asp Arg Cys Arg Ser Lys Tyr Gly Lys
            400                 405                 410

TAT TGG AAG CTG TAT TGT GAG AAA GTC AAA TAC AGG ATC ATT CCG GGA    1359
Tyr Trp Lys Leu Tyr Cys Glu Lys Val Lys Tyr Arg Ile Ile Pro Gly
        415                 420                 425

ATT TAT TGATTGTAAC GAAGTCTGTT GTTCTCATTT TCTACTTATT ACGTTAATTC    1415
Ile Tyr
    430

GAACGTTGGA ATCATCAAAA GACCGAGCCA AAACAAAAAT GCAAATTGAT GCGATAGACA    1475

TTCTTTTGCT GAAAAAAAAA A                                              1496

(2) INFORMATION FOR SEQ ID NO: 2:

(i) SEQUENCE CHARACTERISTICS:
        (A) LENGTH: 430 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Glu Thr Val His Ser Pro Ile Val Thr Tyr Ala Ser Met Leu
1               5                   10                  15
```

```
Ser Leu Leu Ala Phe Cys Pro Pro Phe Val Ile Leu Trp Tyr Thr
            20                  25                  30

Met Val His Gln Asp Gly Ser Val Thr Gln Thr Phe Gly Phe Phe Trp
            35                  40                  45

Glu Asn Gly Val Gln Gly Leu Ile Asn Ile Trp Pro Arg Pro Thr Leu
            50                  55                  60

Ile Ala Trp Lys Ile Ile Phe Cys Tyr Gly Ala Phe Glu Ala Ile Leu
65                  70                  75                  80

Gln Leu Leu Leu Pro Gly Lys Arg Val Glu Gly Pro Ile Ser Pro Ala
                    85                  90                  95

Gly Asn Arg Pro Val Tyr Lys Ala Asn Gly Leu Ala Ala Tyr Phe Val
                100                 105                 110

Thr Leu Ala Thr His Leu Gly Leu Trp Trp Phe Gly Ile Phe Asn Pro
                115                 120                 125

Ala Ile Val Tyr Asp His Leu Gly Glu Ile Phe Ser Ala Leu Ile Phe
                130                 135                 140

Gly Ser Phe Ile Phe Cys Val Leu Leu Tyr Ile Lys Gly His Val Ala
145                 150                 155                 160

Pro Ser Ser Ser Asp Ser Gly Ser Cys Gly Asn Leu Ile Ile Asp Phe
                    165                 170                 175

Tyr Trp Gly Met Glu Leu Tyr Pro Arg Ile Gly Lys Ser Phe Asp Ile
                180                 185                 190

Lys Val Phe Thr Asn Cys Arg Phe Gly Met Met Ser Trp Ala Val Leu
                195                 200                 205

Ala Val Thr Tyr Cys Ile Lys Gln Tyr Glu Ile Asn Gly Lys Val Ser
                210                 215                 220

Asp Ser Met Leu Val Asn Thr Ile Leu Met Leu Val Tyr Val Thr Lys
225                 230                 235                 240

Phe Phe Trp Trp Glu Ala Gly Tyr Trp Asn Thr Met Asp Ile Ala His
                    245                 250                 255

Asp Arg Ala Gly Phe Tyr Ile Cys Trp Gly Cys Leu Val Trp Val Pro
                260                 265                 270

Ser Val Tyr Thr Ser Pro Gly Met Tyr Leu Val Asn His Pro Val Glu
                275                 280                 285

Leu Gly Thr Gln Leu Ala Ile Tyr Ile Leu Val Ala Gly Ile Leu Cys
                290                 295                 300

Ile Tyr Ile Lys Tyr Asp Cys Asp Arg Gln Arg Gln Glu Phe Arg Arg
305                 310                 315                 320

Thr Asn Gly Lys Cys Leu Val Trp Gly Arg Ala Pro Ser Lys Ile Val
                    325                 330                 335

Ala Ser Tyr Thr Thr Thr Ser Gly Glu Thr Lys Thr Ser Leu Leu Leu
                340                 345                 350

Thr Ser Gly Trp Trp Gly Leu Ala Arg His Phe His Tyr Val Pro Glu
                355                 360                 365

Ile Leu Ser Ala Phe Phe Trp Thr Val Pro Ala Leu Phe Asp Asn Phe
370                 375                 380

Leu Ala Tyr Phe Tyr Val Leu Thr Leu Leu Phe Asp Arg Ala Lys
385                 390                 395                 400

Arg Asp Asp Asp Arg Cys Arg Ser Lys Tyr Gly Lys Tyr Trp Lys Leu
                    405                 410                 415

Tyr Cys Glu Lys Val Lys Tyr Arg Ile Ile Pro Gly Ile Tyr
                420                 425                 430

(2) INFORMATION FOR SEQ ID NO: 3:
```

```
    (i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:7
        (D) OTHER INFORMATION:/note= "residue 7 = Trp or Tyr"

(ix) FEATURE:
        (A) NAME/KEY: Peptide
        (B) LOCATION:12
        (D) OTHER INFORMATION:/note= "residue 12 = His or Lys"

(xi) SEQUENCE DESCRIPTION: SEQ ID NO: 3:

Leu Leu Xaa Xaa Gly Trp Xaa Gly Xaa Xaa Arg Xaa Xaa Xaa Tyr
 1               5                  10                  15

(2) INFORMATION FOR SEQ ID NO: 4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE"

(ix) FEATURE:
        (A) NAME/KEY: misc_feature
        (B) LOCATION:10..29
        (D) OTHER INFORMATION:/note= "SEQUENCE ID No 1 FROM 76 TO
             95"

(xi) SEQUENCE DESCRIPTION: SEQ ID NO: 4:

CGCGGATCCA TGGCGGAGAC TGTACATTC                                         29

(2) INFORMATION FOR SEQ ID NO: 5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE"

(ix) FEATURE:
        (A) NAME/KEY: misc_feature
        (B) LOCATION:complement (10..28)
        (D) OTHER INFORMATION:/note= "COMPLEMENTARY SEQUENCE ID
             No 1 FROM 1350 TO 1368"

(xi) SEQUENCE DESCRIPTION: SEQ ID NO: 5:

CAGGGTACCT CAATAAATTC CCGGAATG                                          28

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE"
```

(ix) FEATURE:
            (A) NAME/KEY: misc_feature
            (B) LOCATION:complement (1..23)

(xi) SEQUENCE DESCRIPTION: SEQ ID NO: 6:

GATTACGCCA AGCTTTTCGA AAC                                                     23

(2) INFORMATION FOR SEQ ID NO: 7:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(xi) SEQUENCE DESCRIPTION: SEQ ID NO: 7:

AGATCTTGAG AAGATGCGGC CAGCAAAAC                                               29

(2) INFORMATION FOR SEQ ID NO: 8:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(xi) SEQUENCE DESCRIPTION: SEQ ID NO: 8:

GGGGATCCGT GGTCGACGTA ATTTAGTGTG TGTATTTGTG TTTGCG                            46

(2) INFORMATION FOR SEQ ID NO: 9:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(ix) FEATURE:
            (A) NAME/KEY: misc_feature
            (B) LOCATION:complement (1..17)

(xi) SEQUENCE DESCRIPTION: SEQ ID NO: 9:

GTAAAACGAC GGCCAGT                                                            17

(2) INFORMATION FOR SEQ ID NO: 10:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(xi) SEQUENCE DESCRIPTION: SEQ ID NO: 10:

TTGAAGGTTC AACATCAATT GATTG                                                   25

(2) INFORMATION FOR SEQ ID NO: 11:

(i) SEQUENCE CHARACTERISTICS:

(A) LENGTH: 38 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(ix) FEATURE:
            (A) NAME/KEY: misc_feature
            (B) LOCATION:complement (1..38)

(xi) SEQUENCE DESCRIPTION: SEQ ID NO: 11:

GTGTGGCGGC CGCCTCCTTG TCAATATTAA TGTTAAAG                                  38

(2) INFORMATION FOR SEQ ID NO: 12:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(xi) SEQUENCE DESCRIPTION: SEQ ID NO: 12:

CAAGGAGGCG GCCGCCACAC AAAAAGTTAG GTGT                                      34

(2) INFORMATION FOR SEQ ID NO: 13:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(ix) FEATURE:
            (A) NAME/KEY: misc_feature
            (B) LOCATION:complement (1..25)

(xi) SEQUENCE DESCRIPTION: SEQ ID NO: 13:

TCTGCTTCCC TAGAACCTTC TTATG                                                25

(2) INFORMATION FOR SEQ ID NO: 14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(ix) FEATURE:
            (A) NAME/KEY: misc_feature
            (B) LOCATION:complement (1..20)

(xi) SEQUENCE DESCRIPTION: SEQ ID NO: 14:

TACATTAGGT CCTTTGTAGC                                                      20

(2) INFORMATION FOR SEQ ID NO: 15:

(i) SEQUENCE CHARACTERISTICS:
            (A) LENGTH: 25 base pairs
            (B) TYPE: nucleic acid
            (C) STRANDEDNESS: single
            (D) TOPOLOGY: linear

```
        (ii) MOLECULE TYPE: other nucleic acid
             (A) DESCRIPTION:   /desc = "OLIGONUCLEOTIDE"

(xi) SEQUENCE DESCRIPTION: SEQ ID NO: 15:

GCGCTCAGCG GCCGCTTTCC AGTCG                                                25

(2) INFORMATION FOR SEQ ID NO: 16:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid
             (A) DESCRIPTION:   /desc = "OLIGONUCLEOTIDE"

(xi) SEQUENCE DESCRIPTION: SEQ ID NO: 16:

AATTGCGGCC GCGTACGTAT G                                                    21

(2) INFORMATION FOR SEQ ID NO: 17:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid
             (A) DESCRIPTION:   /desc = "OLIGONUCLEOTIDE"

(ix) FEATURE:
             (A) NAME/KEY: misc_feature
             (B) LOCATION:complement (1..21)

(xi) SEQUENCE DESCRIPTION: SEQ ID NO: 17:

AATTCATACG TACGCGGCCG C                                                    21

(2) INFORMATION FOR SEQ ID NO: 18:

(i) SEQUENCE CHARACTERISTICS:
             (A) LENGTH: 14 base pairs
             (B) TYPE: nucleic acid
             (C) STRANDEDNESS: single
             (D) TOPOLOGY: linear (ii) MOLECULE TYPE: other nucleic acid
             (A) DESCRIPTION:   /desc = "OLIGONUCLEOTIDE"

(xi) SEQUENCE DESCRIPTION: SEQ ID NO: 18:

CAACGCGTCC TAGG                                                            14

(2) INFORMATION FOR SEQ ID NO: 19:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: other nucleic acid
             (A) DESCRIPTION:   /desc = "OLIGONUCLEOTIDE"

(ix) FEATURE:
             (A) NAME/KEY: misc_feature
             (B) LOCATION:complement (1..22)

(xi) SEQUENCE DESCRIPTION: SEQ ID NO: 19:

AATTCCTAGG ACGCGTTGAG CT                                                   22
```

(2) INFORMATION FOR SEQ ID NO: 20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO: 20:

GATCCGCAGA TATCATCTAG ATCCCGGGTA GAT            33

(2) INFORMATION FOR SEQ ID NO: 21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(ix) FEATURE:
        (A) NAME/KEY: misc_feature
        (B) LOCATION:complement (1..39)

(xi) SEQUENCE DESCRIPTION: SEQ ID NO: 21:

AGAGCTCAAG ATCTACCCGG GATCTAGATG ATATCTGCG        39

(2) INFORMATION FOR SEQ ID NO: 22:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO: 22:

CTTGAGCTCT ACGCAGCTGG TCGACACCTA GGAG           34

(2) INFORMATION FOR SEQ ID NO: 23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(ix) FEATURE:
        (A) NAME/KEY: misc_feature
        (B) LOCATION:complement (1..28)

(xi) SEQUENCE DESCRIPTION: SEQ ID NO: 23:

AATTCTCCTA GGTGTCGACC AGCTGCGT                 28

(2) INFORMATION FOR SEQ ID NO: 24:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE"

(xi) SEQUENCE DESCRIPTION: SEQ ID NO: 24:

GCGGATCTGC TCGAAGATTG CCTGCGCGTT GGGCTTGATC                           40

(2) INFORMATION FOR SEQ ID NO: 25:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE"

(xi) SEQUENCE DESCRIPTION: SEQ ID NO: 25:

TCGACGGACG CGTGG                                                      15

(2) INFORMATION FOR SEQ ID NO: 26:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE"

(ix) FEATURE:
        (A) NAME/KEY: misc_feature
        (B) LOCATION:complement (1..14)

(xi) SEQUENCE DESCRIPTION: SEQ ID NO: 26:

TCGACCACGC GTCC                                                       14

(2) INFORMATION FOR SEQ ID NO: 27:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE"

(xi) SEQUENCE DESCRIPTION: SEQ ID NO: 27:

TGGCCGTCGT TTTACTCCTG CGCCTGATGC GGTAT                                35

(2) INFORMATION FOR SEQ ID NO: 28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE"

(xi) SEQUENCE DESCRIPTION: SEQ ID NO: 28:

GGCCGCAAAA CCAAA                                                      15

(2) INFORMATION FOR SEQ ID NO: 29:

(i) SEQUENCE CHARACTERISTICS:

```
            (A) LENGTH: 15 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(ix) FEATURE:
            (A) NAME/KEY: misc_feature
            (B) LOCATION:complement (1..15)

(xi) SEQUENCE DESCRIPTION: SEQ ID NO: 29:

AGCTTTTGGT TTTGC                                                          15

(2) INFORMATION FOR SEQ ID NO: 30:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(xi) SEQUENCE DESCRIPTION: SEQ ID NO: 30:

GATCTATCGA TGCGGCCGCG                                                     20

(2) INFORMATION FOR SEQ ID NO: 31:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(ix) FEATURE:
            (A) NAME/KEY: misc_feature
            (B) LOCATION:complement (1..20)

(xi) SEQUENCE DESCRIPTION: SEQ ID NO: 31:

CGCGCGCGGC CGCATCGATA                                                     20
```

Various modifications of the products and method of the invention may be made without departing from the spirit or scope thereof and it is to be understood that the invention is intended to be limited only as defined in the appended claims.

What is claimed:

1. An isolated cDNA sequence wherein the coding sequence codes for *Arabidopsis thaliana* protein having a delta-5,7 sterol, delta-7 reductase activity and having the nucleotide sequence of SEQ ID No. 1.

2. An expression vector containing a DNA sequence of claim 1.

3. A host cell transformed by a vector of claim 2.

4. An isolated and purified DNA or RNA sequence as obtained by the process of cloning a nucleic acid coding for a protein having a delta-5,7 sterol, delta-7 reductase activity in a microorganism comprising screening with a method selected from the group consisting of
   a) resistance of the microorganism to nystatin or to an analogous compound whose toxicity depends on the presence steroids having a C-7 unsaturated and
   b) the hybridization of the nucleic acid with the nucleotide sequence of SEQ ID No: 1 under average stringency conditions.

5. A host cell transformed by a vector containing a DNA sequence of claim 4.

6. A host cell of claim 3 wherein the host is a yeast or a filamentous fungus.

7. A host cell of claim 5 wherein the host is a yeast or a filamentous fungus.

8. A process for the preparation of a protein having a delta-5,7 sterol, delta-7 reductase activity comprising expressing the protein in a host cell of claim 3, and isolating the expressed protein.

9. The process of claim 8 wherein the host cell is a transformed yeast in which the coding DNA sequence is placed under the control of a yeast promotor.

10. The yeast strain EC01/pCD63 which is deposited at the Collection Nationale de Microorganismes (CNCM) on Feb. 10, 1995 under accession number I-1538.

11. A transformed yeast strain co-expressing *A. thaliana*-Δ-5,7-sterol-Δ-7-reductase (Δ-7-red) cytochrome $P_{450}$ SCC, adrenodoxin reductase (ADR) and adrenodoxine (ADX).

* * * * *